(12) United States Patent
Nicolelis et al.

(10) Patent No.: US 7,209,788 B2
(45) Date of Patent: Apr. 24, 2007

(54) CLOSED LOOP BRAIN MACHINE INTERFACE

(75) Inventors: Miguel A. L. Nicolelis, Chapel Hill, NC (US); John K. Chapin, Atlantic Beach, NY (US); Johan Wessberg, Gothenburg (SE)

(73) Assignee: Duke University, Durham, NC (US)

( * ) Notice: Subject to any disclaimer, the term of this patent is extended or adjusted under 35 U.S.C. 154(b) by 101 days.

(21) Appl. No.: 10/012,012

(22) Filed: Oct. 29, 2001

(65) Prior Publication Data

US 2003/0093129 A1 May 15, 2003

(51) Int. Cl.
*A61N 1/36* (2006.01)
(52) U.S. Cl. .................... 607/48; 607/49; 607/62; 128/905; 600/545; 623/25; 623/57
(58) Field of Classification Search ................. 607/48, 607/49, 2, 45, 46, 62, 116, 117; 623/24, 623/25, 57; 128/905; 600/544, 545, 546, 600/378, 377, 554
See application file for complete search history.

(56) References Cited

U.S. PATENT DOCUMENTS

| | | | |
|---|---|---|---|
| 4,461,304 A | 7/1984 | Kuperstein | |
| 4,569,352 A * | 2/1986 | Petrofsky et al. | 607/49 |
| 4,750,499 A * | 6/1988 | Hoffer | 607/116 |
| 4,760,850 A * | 8/1988 | Phillips et al. | 607/49 |
| 4,808,187 A * | 2/1989 | Patterson et al. | 623/25 |
| 4,878,913 A | 11/1989 | Aebischer et al. | |
| 5,037,376 A | 8/1991 | Richmond et al. | |
| 5,215,088 A | 6/1993 | Normann et al. | |
| 5,314,495 A * | 5/1994 | Kovacs | 623/25 |
| 5,325,865 A | 7/1994 | Beckman et al. | |
| 5,361,760 A | 11/1994 | Normann et al. | |
| 5,413,611 A * | 5/1995 | Haslam et al. | 623/25 |
| 5,617,871 A | 4/1997 | Burrows | |
| 5,638,826 A | 6/1997 | Wolpaw et al. | |
| 5,687,291 A | 11/1997 | Smyth | |
| 5,692,517 A | 12/1997 | Junker | |
| 5,735,885 A | 4/1998 | Howard, III et al. | |
| 5,758,651 A | 6/1998 | Nygard et al. | |
| 5,843,142 A | 12/1998 | Sultan | |
| 5,855,801 A | 1/1999 | Lin et al. | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |

(Continued)

OTHER PUBLICATIONS

Kensall D. Wise et al., "An Integrated-Circuit Approach to Extraceullar Microelectrodes;" IEEE Transactions on Biomedical Engineering, vol. BME-17, No. 3, Jul. 1970, pp. 238-247.

(Continued)

*Primary Examiner*—Kennedy Schaetzle
(74) *Attorney, Agent, or Firm*—Jenkins, Wilson, Taylor & Hunt, P.A.

(57) ABSTRACT

A closed loop brain-machine interface is disclosed. The closed loop brain-machine interface translates one or more neural signals into a movement, or a series of movements, performed by a machine. The close-loop brain-machine interface also provides sensory feedback to the subject. Methods of employing the closed loop brain-machine interface are also disclosed.

62 Claims, 24 Drawing Sheets

U.S. PATENT DOCUMENTS

| | | | |
|---|---|---|---|
| 6,001,065 | A | 12/1999 | DeVito |
| 6,006,124 | A | 12/1999 | Fischell et al. |
| 6,016,449 | A | 1/2000 | Fischell et al. |
| 6,024,700 | A | 2/2000 | Nemirovski et al. |
| 6,024,702 | A | 2/2000 | Iversen |
| 6,027,456 | A | 2/2000 | Feler et al. |
| 6,038,477 | A | 3/2000 | Kayyali |
| 6,042,555 | A * | 3/2000 | Kramer et al. ............... 600/595 |
| 6,061,593 | A | 5/2000 | Fischell et al. |
| 6,092,058 | A | 7/2000 | Smyth |
| 6,113,553 | A | 9/2000 | Chubbuck |
| 6,125,300 | A | 9/2000 | Weijand et al. |
| 6,128,538 | A | 10/2000 | Fischell et al. |
| 6,134,474 | A | 10/2000 | Fischell et al. |
| 6,154,678 | A | 11/2000 | Lauro |
| 6,161,045 | A | 12/2000 | Fischell et al. |
| 6,163,725 | A | 12/2000 | Peckham et al. |
| 6,169,981 | B1 | 1/2001 | Werbos |
| 6,171,239 | B1 * | 1/2001 | Humphrey ................... 600/372 |
| 6,175,762 | B1 | 1/2001 | Kirkup et al. |
| 6,181,965 | B1 | 1/2001 | Loeb et al. |
| 6,185,455 | B1 | 2/2001 | Loeb et al. |
| 6,216,045 | B1 | 4/2001 | Black et al. |
| 6,240,315 | B1 | 5/2001 | Mo et al. |
| 6,254,536 | B1 | 7/2001 | DeVito |
| 6,280,394 | B1 | 8/2001 | Maloney et al. |
| 6,353,754 | B1 | 3/2002 | Fischell et al. |
| 6,354,299 | B1 | 3/2002 | Fischell et al. |
| 6,358,202 | B1 | 3/2002 | Arent |
| 6,360,122 | B1 | 3/2002 | Fischell et al. |
| 6,427,086 | B1 | 7/2002 | Fischell et al. |
| 6,459,936 | B2 | 10/2002 | Fischell et al. |
| 6,466,822 | B1 | 10/2002 | Pless |
| 6,473,639 | B1 | 10/2002 | Fischell et al. |
| 6,480,743 | B1 | 11/2002 | Kirkpatrick et al. |
| 6,500,210 | B1 * | 12/2002 | Sabolich et al. ............... 623/24 |
| 6,615,076 | B2 * | 9/2003 | Mitra et al. .................. 600/544 |
| 2001/0023368 | A1 | 9/2001 | Black et al. |
| 2001/0027338 | A1 | 10/2001 | Gielen et al. |
| 2001/0029391 | A1 | 10/2001 | Gluckman et al. |
| 2001/0051819 | A1 | 12/2001 | Fischell et al. |
| 2001/0056290 | A1 | 12/2001 | Fischell et al. |
| 2002/0002390 | A1 | 1/2002 | Fischell et al. |
| 2002/0013612 | A1 | 1/2002 | Whitehurst |
| 2002/0016638 | A1 | 2/2002 | Mitra et al. |
| 2002/0099412 | A1 | 7/2002 | Fischell et al. |
| 2002/0169485 | A1 | 11/2002 | Pless et al. |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly In Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use In Extracellular Neurophysiology," IEEE Transactions on Biomedical Engineering, vol. BME-22, No. 3, May 1975, pp. 212-219.

V.B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity In the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al.; "A Glass/Silicon Composite Intracortical Electrode Array," Annals of Biomedical Engineering. vol. 20, 1992, pp. 423-437.

Reinhard Eckhorn et al., "A new method for the insertion of multiple microprobes into neural and muscular tissue, including fiber electrodes, fine wires, needles and microsensors," Journal of Neuroscience Methods, vol. 49, 1993, pp. 175-179.

Craig T. Nordhausen et al., "Optimizing recording capabilities of the Utah Intracortical Electrode Array," Brain Research, vol. 637, Nos. 1/2, Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institute of Neurological Disorders and Stroke, National Institutes of Health, Electroencephalography and Clinical Neurophysiology, No. 93, 1994, pp. 390-403.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D. M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing-Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time Implementation of electromyogram pattern recognition as a control command of man-machine interface," Medical Engineering Phys., vol. 18, No. 7, 1996, pp. 529-537.

P. Nisbet, "Integrating assistive technologies: current practices and future possibilities," Med. Eng. Phys., vol. 18, No. 3, 1996, pp. 193-202.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P. R. Kennedy et al., "Restoration of neural output from a paralyzed patient by a direct brain connection," NeuroReport, vol. 9, No. 8, Jun. 1998, pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Gregor Rainer et al., "Prospective Coding for Objects in Primate Prefrontal Cortex," The Journal of Neuroscience, vol. 19, No. 13, Jul. 1, 1999, pp. 5493-5505.

Mijail Serruya et al., "Robustness of neuroprosthetic decoding algorithms," Biological Cybernetics, 2003, pp. 1-10.

Nicolelis et al., "Induction of Immediate Spatiotemporal Changes in Thalamic Networks by Peripheral Block of Ascending Cutaneous Information," Nature, p. 533-536, (Feb. 1993).

Nicolelis et al., "Spatiotemporal Structure of Somatosensory Responses of Many-Neuron Ensembles in the Rat Ventral Posterior Medial Nucleus of the Thalamus," Journal of Neuroscience, p. 3511-3532, (Jun. 1994).

Nicolelis et al., "Reconstructing the Engram: Simultaneous, Multisite, Many Single Neuron Recordings," Neuron, p. 529-537, (Apr. 1997).

Owens et al., "Multi-electrode Array for Measuring Evoked Potentials from Surface of Ferret Primary Auditory Cortex," Journal of Neuroscience Methods, p. 209-220, (May 1995).

Summerlee et al., "The Effect of Behavioural Arousal on the Activity of Hypthlamic Neurons in Unanaesthetized, Freely Moving Rats and Rabbits," Proceedings of the Royal Society of London Series B-Biological Sciences, p. 263-272, (Jan. 1982).

Notification of Transmittal of International Preliminary Examination Report dated Aug. 2, 2004.

Written Opinion for corresponding PCT Application No. PCT/US02/31269 dated Mar. 29, 2004.

* cited by examiner

CLOSED LOOP BRAIN MACHINE INTERFACE

GOVERNMENT RIGHTS

This invention was made with Government support under contract 313-4073 awarded by DARPA and grants R01-NS40543 and N01-NS62352, awarded by NIH. Therefore, the Government has certain rights in this invention.

TECHNICAL FIELD

The present invention relates generally to an interface between a machine and a patient's brain, and more particularly to an interface between one or more types of neural signals originating in the brain of a patient. The signals are transmitted to a responsive mechanical device, which, in turn, relays sensory feedback to the patient. The present invention further generally relates to methods by which one or more neural signals originating in a subject's brain are converted to motion in a mechanical device.

| Abbreviations | |
|---|---|
| ANN | artificial neural network |
| DSP | digital signal processing |
| EEG | electroencephalograph |
| fMRI | functional magnetic resonance imaging |
| LAN | local area network |
| M1 | primary motor cortex |
| MNAP | many neuron acquisition processor |
| PMd | dorsal premotor cortex |
| PP | posterior parietal cortex |
| RMS | root mean square |
| SRAM | static random access memory |
| TCP/IP | transmission control protocol/internet protocol |

BACKGROUND ART

The human brain is an exceedingly complex processing system, which integrates continual streams of incoming sensory input data with stored memories, uses the input data and memories in complex decision processes at both conscious and unconscious levels and, on the basis of these processes, generates observable behaviors by activation of its motor or movement control pathways and the muscles which these innervate.

In certain cases of traumatic injury or neurological disease, however, the brain is partially isolated from the periphery. Input data from certain senses are thus lost, at least for a portion of the body, as are many voluntary movements. Spinal cord injury is a well-known example. With spinal cord injury, the pathways that link higher motor centers in the brain with the spinal cord and that are used for control of voluntary movements can be functionally transected at the site of injury. As a result, the patient is paralyzed, and can no longer voluntarily activate muscles that are innervated by regions of the spinal cord below the level of the injury. Despite the injury to their long fibers, however, many of the cells in these higher brain regions that control voluntary movement will survive and can still be activated voluntarily to generate electric signals for controlling voluntary movement. By recording the electrical activities produced from these cells with implantable devices (e.g., a microwire electrode array or a microwire), signals generated by the cells can be "exteriorized" and used for the control of external prostheses, such as an assist robot or an artificial limb, or functional electrical stimulation paralyzed muscles.

Another example of such loss occurs in cases of amyotrophic lateral sclerosis (Lou Gehrig's Disease), in which the motor neurons that control muscles, as well as some of the brain cells that control these motor neurons, degenerate. In advanced stages of this disease, the patient might have completely intact senses and thought processes, but is "locked in," so that neither movements nor behavioral expressions of any kind can be made. Providing these patients with some way of communicating with the external world would greatly enhance their quality of life.

In sum, there is a need to develop a system for monitoring and processing the electrical signals from neurons within the central nervous system, so that the brain's electrical activity can be "exteriorized" and used for the voluntary control of external prostheses or assist devices which are adapted to provide sensory feedback. In this way, damaged pathways are circumvented and some control of the environment can be restored, as well as impart to a patient the ability to interact with his or her environment. Because the electrical fields of small groups of neurons drop off rapidly with distance from the cells, a suitable system preferably includes surgically implanted electrodes or sensors, which can be placed in close proximity to the individual brain cells that generate command signals for voluntary movement.

Earlier attempts to utilize signals recorded directly from neurons for the express purpose of controlling an external actuator have, however, encountered a number of technical difficulties. One problem is how to obtain stable electrical signals of sufficient amplitude and temporal resolution for real-time control of an external device. Previous approaches have been used, but have been unsuccessful in this regard. Additionally, prior to the disclosure of the present invention, it was not possible for a patient to control the complex one- or three-dimensional complex trajectory of an external actuator via neural signals that was adapted to provide sensory feedback to the patient.

In recent years, small, multichannel, micromachined electrodes have been developed for use in neural recording. Given sufficient recording channel density, these electrodes offer a solution to the electrode/tissue movement problem described above. Another approach is to employ electrodes with larger exposed recording surfaces (in the range of 0.5 to 1.5 mm$^2$ in surface area). These low impedance electrodes have lower noise characteristics than those with smaller tips, and can reliably record the activity of hundreds to thousands of single cortical neurons. Indeed, low level electroencephalographic (EEG) or other brain-derived neural signal information can even be recorded from the surface of the scalp. This approach can thus avoid the difficulty of different signal output levels caused by small movements between the electrodes and the selected cells encountered in the first approach.

The use of the signals recorded in the second approach, however, presents a major problem for actuator control. In such recordings, the desired control signals can be of very low amplitude and can be "buried" within, or confounded by, EEG potentials from neurons that are not involved in voluntary motor processes. Thus, averaging must be used over many movement attempts to extract a usable signal and the extracted signal cannot be employed to reproduce a time-varying arm trajectory. For this reason, this approach is less than desirable and perhaps not useful for real-time neural control of an external device.

Another problem, which occurs regardless of the electrode type used, is that neural signals can change over time for a variety of reasons, such as naturally occurring cell death, which occurs randomly throughout the brain in adults and learning processes, which might, over time, alter the quantitative relationship between a neuron's activity and the external parts of the body to which it contributes voluntary control.

Additionally, prior art apparatuses and methods have not addressed the closure of the "sensory loop" between the brain and the actuator. That is, even if a prior art apparatus or method could control an actuator by employing the brain signals of a subject, there is no sensory feedback from the actuator to the brain of the subject; the subject is not supplied with tactile and other sensory information acquired by the actuator. For example, if a patient directs an actuator to grasp an object and the actuator does grasp the object, the subject still does not know, for example, if the object is hard or soft, rough or smooth or hot or cold. This inability represents yet another limitation of prior art apparatuses and methods.

The methods and apparatuses described herein are adaptable to a variety of signals from the brain or central nervous system such as brain-derived electrical signals, acquired via microelectrode technologies from within the brain. The external devices can comprise any device that can be controlled by processed brain-derived electrical signals. These devices include, but are not limited to, artificial or prosthetic limbs; computer controlled, functional electrical stimulation of muscles of paralyzed individuals for the restoration of movement; robots or robotics components; computers or computer displays; or the teleoperation of robots and machines in hostile environments.

What is needed, therefore, is a closed loop brain-machine interface that can translate neural signals in the brain of a subject into movement of an external device, the external device adapted to provide sensory feedback to the subject. The present invention solves these and other problems associated with methods and apparatuses for obtaining signals directly from the brain or central nervous system, for processing and utilizing these signals to control one or more external devices, such as an actuator, and for providing a subject with sensory feedback from the external devices.

SUMMARY OF THE INVENTION

A real time closed loop brain-machine interface is disclosed. In a preferred embodiment, the real time closed loop brain-machine interface comprises: (a) a plurality of electrodes adapted to be chronically implanted in the nervous system of a subject and to acquire extracellular electrical signals from a population of individual neural cells; (b) a signal processing mechanism adapted to form extracted motor commands from the extracellular electrical signals, the signal processing mechanism adapted to communicate with the plurality of electrodes; and (c) an actuator adapted to respond to the extracted motor commands by effecting a movement, to provide sensory feedback to the subject. Preferably, the signal processing mechanism comprises: (a) one or more neurochips adapted to be chronically implanted in the body of a subject in communication with the plurality of electrodes; (b) a data acquisition module in communication with the one or more neurochips; (c) a motor command extraction module in communication with the data acquisition module; and (d) a power supply for relaying power to the neurochip and transmitting signals received at the neurochip to the data acquisition module.

A real time closed loop brain-machine interface for restoring voluntary motor control and sensory feedback to a subject that has lost a degree of voluntary motor control and sensory feedback is also disclosed. In a preferred embodiment, the apparatus comprises: (a) an implantable microwire electrode array adapted to acquire one or more brain-derived neural signals; (b) an implantable neurochip adapted to filter and amplify the one or more brain-derived neural signals, the implantable neurochip adapted to communicate with the implantable microwire array; (c) a motor command extraction microchip embodying one or more motor command extraction algorithms, the microchip adapted to communicate with the implantable neurochip and the algorithms adapted to extract motor commands; (d) an actuator adapted to move in response to the motor commands and to acquire sensory feedback information during and subsequent to a movement, the actuator further adapted to communicate with the motor command extraction microchip; (e) a sensory feedback microchip embodying one or more sensory feedback information interpretation algorithms, the sensory feedback microchip adapted to communicate with the actuator and the one or more sensory feedback information interpretation algorithms, the sensory feedback microchip adapted to form interpreted sensory feedback information; (f) a structure adapted to deliver interpreted sensory feedback information to the subject, the structure adapted to communicate with the sensory feedback microchip; and (g) one or more power sources adapted to provide power to the implantable neurochip, the motor command extraction microchip, the actuator, the sensory feedback microchip, the structure adapted to relay interpreted sensory feedback information to the subject or a combination thereof.

Additionally, a method of controlling an actuator adapted to provide sensory feedback to a subject by neural signals is disclosed. In a preferred embodiment, the method comprises: (a) collecting a neural signal from the nervous system of a subject; (b) processing the neural signal to form a processed neural signal; (c) extracting one or more motor commands from the processed neural signal to form an extracted motor command; (d) transmitting the extracted motor command to an actuator, whereby the actuator effects a movement; (e) acquiring sensory feedback information from the actuator; (f) interpreting the sensory feedback information to form interpreted sensory feedback; information; and (g) relaying the interpreted sensory feedback information back to the subject. Preferably, the processing comprises: (a) amplifying the one or more neural signals to form amplified neural signals; (b) filtering the amplified neural signals to form filtered neural signals; and (c) performing a spike detection analysis on the filtered neural signals.

A method of imparting voluntary motor control and sensory feedback to a subject that has lost a degree of voluntary motor control and sensory feedback is also disclosed. In a preferred embodiment, the method comprises: (a) implanting a neural signal acquisition apparatus in the tissue of a subject's central nervous system; (b) fitting the subject with an actuator adapted to respond to neural signals with movement and to acquire sensory feedback; (c) collecting one or more neural signals; (d) extracting one or more motor commands from the acquired neural signals to form extracted motor commands; (e) transmitting the extracted motor commands to the actuator; (f) effecting a movement corresponding to the extracted motor commands; (g) acquiring sensory feedback information via the actuator; (h) interpreting the sensory feedback information to form interpreted sensory feedback information; and (i) relaying the interpreted sensory feedback information to the subject, whereby voluntary motor control and sensory feedback is imparted to a subject that has lost a degree of voluntary motor control and sensory feedback. Preferably, the neural signal acquisition apparatus comprises: (a) a plurality of electrodes; and (b) a neurochip adapted to amplify and filter neural signals the neurochip adapted to communicate with the plurality of electrodes.

Accordingly, it is an object of the present invention to provide a closed loop brain-machine interface. The object is achieved in whole or in part by the present invention.

An object of the invention having been stated hereinabove, other objects will be evident as the description proceeds, when taken in connection with the accompanying Drawings and Laboratory Examples as best described hereinbelow.

DETAILED DESCRIPTION OF THE INVENTION

Figure 1A:
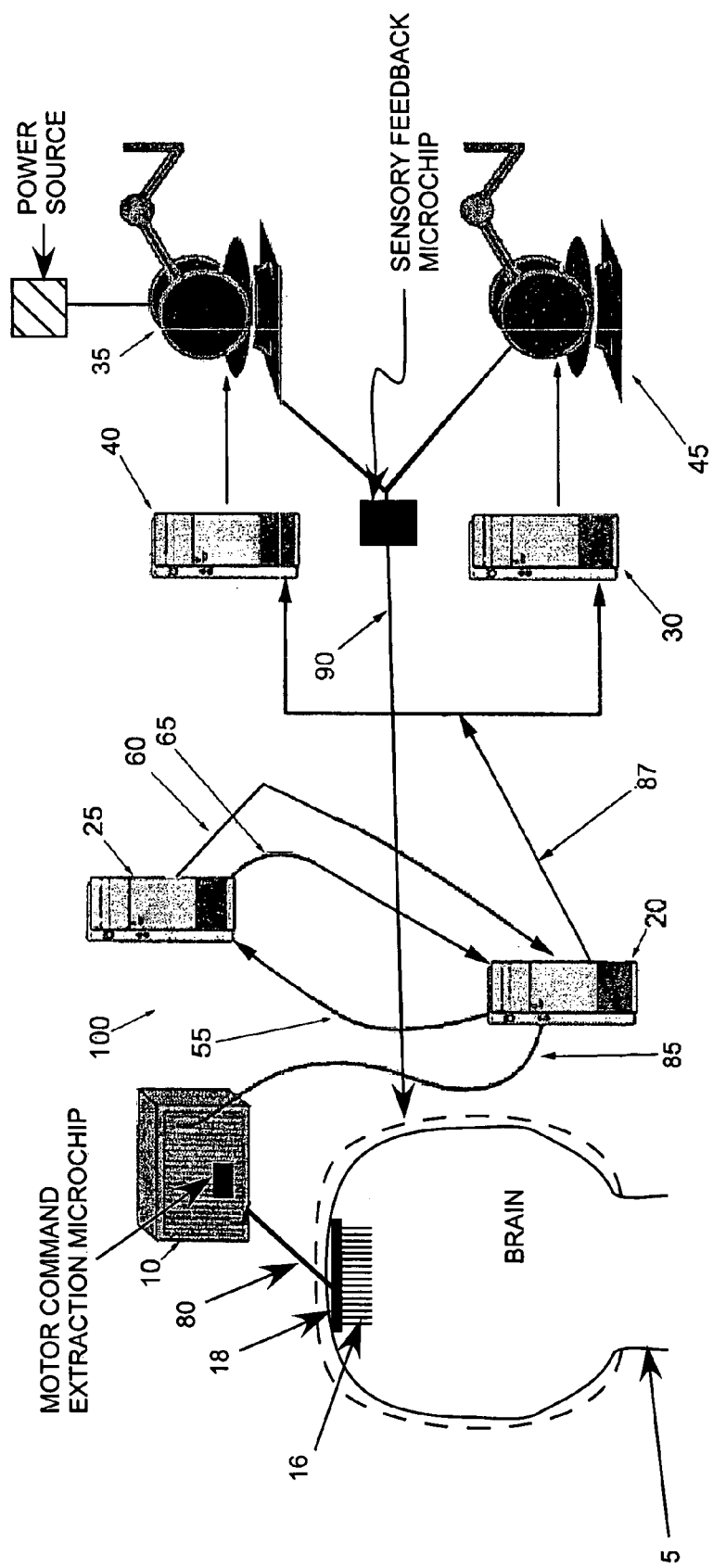
FIG. 1A is a schematic drawing representing a preferred embodiment of a brain-machine interface.

The present invention comprises a closed loop brain-machine interface that employs brain-derived signals and can be utilized to restore motor functions in patients with severe degrees of paralysis. Additionally, the closed loop brain-machine interface provides sensory feedback to the subject employing the apparatus. The closed loop brain-machine interface is an advance beyond prior art apparatuses, methods and propositions in the fields of neurology and neuroprosthetics because it can employ one or more chronically-implanted arrays of microwires to acquire the type of brain-derived motor commands that can control the movements of an actuator adapted to perform a series of tasks and to provide sensory feedback to the subject, thereby closing the brain-actuator control loop. The closed loop aspect of the brain-machine interface represents one particular advance beyond prior art apparatuses and methods because it closes the brain-actuator loop by providing sensory feedback from the actuator to the brain, thereby offering severely paralyzed and otherwise motor-impaired patients the ability to receive sensory feedback from a prosthetic limb. This ability has been heretofore unavailable.

In one embodiment of the closed loop brain-machine interface, chronically implanted arrays of microwires sample the extracellular electrical activity of a plurality of single neurons, distributed across a variety of motor cortical areas, such as the primary motor cortex, dorsal and ventral premotor areas, and the medial supplementary motor cortex, the somatosensory cortex and a group of posterior parietal areas that define a large neural network involved in the generation of motor commands for visually-guided arm reaching movements. These brain-derived electrical signals are conditioned through a dedicated microchip (i.e. an implantable neurochip), which forms a component of the present invention.

Broadly, this dedicated microchip facilitates the telemetry of large-scale digitized information from the simultaneously acquired cortical motor neurons that feeds one or more real-time algorithms, which can be running on one or more conventional computers, that are capable of extracting motor commands capable of controlling the 3-D movements of an actuator. Signals defining the x, y, and z-axes of the actuator are extracted from these brain-signals and transmitted to the actuator. The actuator, in turn, moves according and provides sensory feedback, such as tactile information, back to the subject in or on which the closed loop brain-machine interface is implanted.

I. Definitions

Following long-standing patent law convention, the terms "a" and "an" mean "one or more" when used in this application, including the claims.

As used herein, the terms "actuator", "external device" and "prosthetic limb" are used interchangeably and mean any kind of device adapted to perform a movement. Although an actuator preferably performs a movement in three dimensions, an actuator can also be limited to performing movements in two dimensions. Thus, an actuator can be a manipulandum confined to two-dimensional motion. A preferred actuator comprises a prosthetic limb, which can be fitted on, or integrated into, the body of a subject. An actuator can also be associated with machinery and/or circuitry that allow the actuator to respond to one or more forms of input with one or more movements. It is also preferable that the range of motion of an actuator designated as a substitute for a patient's lost or paralyzed limb be limited to the range of motion of the limb for which the actuator is substituting.

As used herein, the term "artificial neural network" means a computational algorithm, implemented with software or hardware, that is capable of extracting a motor command from a spatio-temporal pattern of brain activity.

As used herein, the term "digital signal processor" means a device adapted to perform one or more operations on digital data relayed to the digital signal processor. A digital signal processor can comprise an analog-to-digital converter adapted to convert analog signals, such as raw neural signals, to a digital form.

As used herein, the term "electrode" means an electric conductor through which an electric current can pass. An electrode can also be a collector and/or emitter of an electric current. Preferably, an electrode is a solid and comprises a conducting metal. Preferable conducting metals include noble metals, alloys and particularly stainless steel and tungsten. An electrode can also be a microwire, or the term "electrode" can describe a collection of microwires. Thus, particularly preferred electrodes comprise TEFLON® coated stainless steel or tungsten microwires.

As used herein, the term "extracellular electrical signal" means an electrical signal that independently exists outside of the membrane or wall of a cell. An extracellular electrical signal can, however, originate in a cell, such as one or more neural cells. An extracellular electrical signal is contrasted with an intracellular electrical signal, which originates, and remains, in a cell. An extracellular electrical signal can comprise a collection of extracellular electrical signals generated by one or more cells.

As used herein, the term "linear model" is defined as a model in which one or more dependent variables (e.g., x, y and/or z trajectories) result from the linear weighted sum of the values of one or more independent variables (e.g., individual single neurons).

As used herein, the term "many neuron acquisition processor" means a device adapted to receive and perform one or more operations on neural signals relayed to the many neuron acquisition processor.

As used herein, the term "microwire" means a metal wire of having a diameter of between about 10 and about 75 µm. Preferably, a microwire is TEFLON® coated.

As used herein, the terms "microwire electrode array" and "microwire array" are used interchangeably and mean a collection of two or more microwires arranged in a fixed spatial relationship to one another, with the microwires having a first and a second end. The first end of a microwire is preferably, but is not required to be, adapted to interact with neural tissue and the second end is preferably disposed in electrical communication with a neurochip, the neurochip adapted to accommodate signals acquired by each microwire of a microwire array. An individual microwire of a microwire array does not typically contact another microwire of the microwire array at any point. Preferably the second end of the each microwire is maintained in a fixed spatial relationship with other microwires of the microwire array.

As used herein, the terms "microwire electrode bundle" and "microwire bundle" are used interchangeably and mean a collection of two or more microwires arranged in a fixed spatial relationship to one another, with the microwires having a first and a second end. The first end of a microwire is preferably, but is not required to be, adapted to interact with neural tissue and the second end is preferably disposed in electrical communication with a neurochip, the neurochip adapted to accommodate signals acquired by each microwire of a microwire bundle. An individual microwire of a microwire bundle typically contacts at least one other microwire of the microwire bundle. Preferably, the lengths of each microwire of a microwire bundle are of different lengths. A microwire electrode bundle differs from a microwire electrode array at least in that in a bundle, the microwires are in close contact. In an array, the microwires can be separated from one another.

As used herein, the term "motor command" means one or more neural signals associated with the control of one or more muscles or muscle groups of a subject. Motor commands are generally formed in the brain or nervous system of a subject and these commands control movements executed by the muscles of the subject. Movements preferably comprise voluntary movements, however movements can also comprise involuntary movements.

As used herein, the terms "movement trajectory" and "trajectory" are used interchangeably and mean a path in space through which an object, such as an actuator or the appendage of a subject, travels. The term also refers to the path the actuator or appendage is desired or directed to travel.

As used herein, the term "multiplex" means the action of combining two or more signals for the purpose of relaying the signals over a single line or media.

As used herein, the term "neurochip" means any microchip adapted for implantation in the body of an organism. Preferably, a neurochip is adapted to be implanted in the nervous system of an organism.

As used herein, the term "neural signal" means a signal, which can take any form, originating in the nervous system of an organism.

As used herein, the terms "operator", "patient" and "subject" are used interchangeably and mean any individual monitoring or using the present invention. Operators can be researchers gathering data from an individual, an individual who determines the parameters of operation of the present invention or the individual in or on which the intelligent brain pacemaker is disposed. Broadly, then, an "operator", "patient" or "subject" is one who is employing the present invention for any purpose. As used herein, the terms "operator", "patient" and "subject" need not refer exclusively to human beings, but rather the terms encompass all organisms suffering from some degree of loss of motor control. Preferably, the terms refer to mammals and more preferably to humans. "Patients" and "subjects" are preferably organisms in which the present invention is being employed.

As used herein, the terms "sensory feedback", "sensory feedback information" and "sensory feedback data" are used interchangeably and mean any form of data relating to the perception by, or interaction between, an actuator and an object. Sensory feedback can take the form of tactile information such as shape, hardness and brittleness or sensory feedback can take the form of temperature information, such as hot or cold. Tactile information can also relate to the amount of force applied by an actuator to an object.

As used herein, the term "spike discrimination program" means software adapted to analyze and identify a waveform or series of data in order to identify repetitive and/or non-repetitive variations in action potentials of single brain cells, which constitute the raw neural signal employed to control an actuator. Preferably, a waveform comprises neural signals. Preferably, a spike discrimination program is adapted to perform waveform analysis functions including, but not limited to signal averaging, RMS amplitude determinations waveform discrimination and various forms of spectral analysis. Preferably, criteria for identifying repetitive and/or non-repetitive variations in the waveform can be set by an operator and thereby, permit the user to apply stringent or less stringent conditions in the identification of an amplitude variation.

As used herein, the term "timing board" means circuitry, which can be embodied on a circuit board, adapted to coordinate one or more events as a function of time. For example, a timing board can be adapted to direct an event to occur at regular intervals and send a signal intended to initiate the occurrence of that event.

II. General Considerations

Through the years there has been significant research in the area of detecting and observing various electric potentials generated within the human body for medical diagnosis, biofeedback control of mental and physical states, and control of external devices. It is known that different regions of the brain are used to control different parts of the body and to process different sensory inputs. It is also known that when a human performs a certain function, such as moving an extremity or listening to a particular sound, multiple regions of the brain generate electrical action potentials to accomplish that function. It is also known that direct electrical stimulation of a particular region of the brain can cause at least partial reproduction of the functions or sensory input normally associated with that region of the brain. Determining which portions of a patient's brain are responsible for certain motor activities or certain sensory functions has become known as brain "mapping." In theory, after a patient's brain has been mapped, the brain can be electrically stimulated to restore lost functions.

For example, it is possible to determine which portions of a patient's brain are responsible for processing signals associated with the movement of an extremity. Once a neurosurgeon knows which portions of the patient's brain are responsible for processing these signals, it is possible to electrically stimulate selected portions of the patient's brain to cause the patient to "move" the extremity. Thus, a patient whose motor control has been partially or permanently damaged can regain motor control if an apparatus is employed to translate these neural signals into movement of an external device, such as an actuator. Similarly, if the areas of the patient's brain that are associated with tactile and other sensory information are known, these areas of the patient's brain can be electrically stimulate to make the patient "experience" the sensory interaction between an object and an external device interacting with the object. The closed loop brain-machine interface makes these and other goals possible and can greatly enhance the quality of life of those individuals whose motor control has been impaired.

III. Configuration and Operation of the Closed Loop Brain-machine Interface

FIG. 1A is a schematic drawing of one embodiment of the closed loop brain-machine interface of the present invention, generally designated 100. This embodiment of the present invention generally comprises subject 5, data acquisition unit 10, server 20, analysis computer 25, local client computer 30 associated with robot arm 35 and remote client computer 40 associated with robot arm 45.

Referring again to the embodiment depicted in FIG. 1A, a more detailed description of the how the closed loop brain machine interface is configured and operates is as follows. Initially, one or more microwire electrodes, which can comprise microwire electrode arrays or bundles of microwire electrodes 16 adapted to acquire neural signal data are implanted in the brain of subject 5. Preferably, each of the one or more microwire electrodes, such as those electrodes comprising a microwire electrode array or bundle, is implanted in one or more different cortical areas of the brain of subject 5.

The one or more microwire electrodes acquire neural signals from the brain of subject 5, which preferably take the form of a plurality of electrical signals known as action potentials. Neural signals preferably comprise extracellular electrical signals. Acquired neural signals generally comprise motor commands originating in the brain of subject 5, although acquired neural signal data can encode other components as well. In fact, an advantage of the closed loop brain machine interface is that it can deconvolute complex neural signal data and extract motor command components from a collection of acquired neural signals.

Specifically, combined neural signals can code for a three-dimensional trajectory through which the subject directs its body, or a component of its body, to follow. For example, a trajectory can correspond to the path followed by a subject's arm, and the trajectory followed by the arm will be encoded by a composite of neural signals. The precise nature of the motor commands can vary, although suitable motor commands will typically comprise signals directing one or more of the subject's arms, legs or other appendage to follow a certain three-dimensional trajectory.

As neural signal data is gathered, it is transmitted to one or more implanted neurochips 18. Neurochip 18 or neurochips 18 are implanted within the body of the subject, and is preferably adapted to be attached to the interior or exterior of the subject's skull. Neurochip 18 preferably amplifies, filters and multiplexes the acquired neural signals. Neurochip 18 is in direct electrical communication with the electrodes. Electrical communication can be achieved, for example, via an array of electrode contact pads mounted on neurochip 18 for receiving the electrodes. Preferably, each electrode is received individually by one of the electrode contact pads, and the electrode contact pads are electrically isolated from each other.

While and after neural signal data is amplified and filtered, it is transmitted from neurochip or neurochips 18 to data acquisition unit 10. Transmission of neural signal data can be by means of a hardline, such as cable 80, however transmission is preferably accomplished via a telemetric method or other wireless mechanism. Transmission of neural signal need not be directly to data acquisition unit 10, and the data can be first transmitted to another component, such as a computer, before it is transmitted to data acquisition unit 10. Transmission can be wireless or it can be via a cable, such as cable 85.

Data acquisition unit 10 receives the amplified and filtered neural signals, performs any additional data processing desired and subsequently transmits the processed neural signals to server 20. Although server 20 is depicted in FIG. 1A, the processed neural signals do not need to be relayed to a server and can instead be transmitted from a data acquisition unit directly to a processing unit. Data acquisition unit 10 preferably comprises an MNAP, which can be employed to acquire and distinguish signals between single neurons. As an aspect of distinguishing between single neurons, the source of a given neuron can be identified. For example, a data acquisition unit can identify a neural signal originating in a subject's posterior parietal cortex and distinguish that signal from a signal originating in a subject's primary motor cortex. Data acquisition unit 10 preferably comprises one or more timing boards, which regulate and identify temporal aspects of the neural signals, and one or more digital signal processors (DSPs), which perform any desired signal processing. Thus, data acquisition unit 10 preferably collects neural data, identifies the source of the various data components, performs any desired signal processing and subsequently transmits the data to server 20. In FIG. 1A, the data path between server 20 and data acquisition unit 10 is represented by data path 85. Transmission of the data can be accomplished via a cable or by a telemetric or other wireless method.

Server 20 fulfills the role of a data hub and operates to receive and route processed neural signals. In the configuration depicted in FIG. 1A, server 20 receives the processed neural signals from data acquisition unit 10 and relays this data to processing computer 25. Server 20 is adapted to also receive data from processing computer 25 and to retransmit data to one or more client computers.

As noted, server 20 operates to transmit neural signal data from data acquisition unit 10 to processing computer 25. Again, this can be via a cable or can be accomplished by wireless transmission. When the neural signal data arrives at processing computer 25, motor command data is extracted. Motor command data is extracted by operating on the processed neural signals with one or more algorithms. The extraction process performed on processing computer 25 generates a correlation between the brain-derived neural data directing a subject's body to perform a given motion and the trajectory the subject's body will follow. That is, processing computer 25 and the algorithms disposed thereon operate on the neural signals originating in the brain of a subject; the motor commands encoded by the neural signals are extracted and translated into a series of spatial coordinates through which the subject desires its body to move. In effect, the algorithms disposed on processing computer 25 generate a "prediction" of the trajectory through which the subject is directing his or her body to travel. In the configuration depicted in FIG. 1A, both linear and an artificial neural network (ANN) models are employed to extract a trajectory prediction from neural signal data. In operation, processing computer 25 can also comprise the components of a server, thereby eliminating the need for server 20.

When one or more motor commands have been extracted from processed neural signals, the extracted motor commands are transmitted back to server 20. FIG. 1A depicts data paths from processing computer 25 to server 20 for motor commands extracted by a linear model (65) and an ANN model (60). Again, data can be transmitted via a cable or via telemetry or other wireless manner.

Continuing with FIG. 1A, when server 20 receives the motor commands from processing computer 25, it transmits the extracted motor commands to one or more client computers. Client computers can be local or remote. When a client computer is remote, transmission of extracted motor commands can be achieved via the Internet, following standard transmission control protocol/internet protocol (TCP/IP) protocols. When a client computer is local, transmission can be achieved via a local area network (LAN). Referring again to the embodiment disclosed in FIG. 1A, extracted motor commands are transmitted via data path 87 to local client computer 30 and remote client computer 40. When both local and remote client are employed, transmission can be simultaneous or alternating.

Actuator 35 is associated with client computer 30 and actuator 45 is associated with client computer 40, as depicted in FIG. 1A. Each actuator associated with a client is adapted to translate extracted motor commands into movement commands to which an associated actuator can respond. Actuator control can be achieved via a software control program. Suitable control programs can be supplied with the actuator, if it is purchased commercially, or a suitable control program can be written de novo in a programming language such as C++. Alternatively, a robot can be configured to respond to trajectory prediction data directly via onboard circuitry and/or firmware.

A client and one or more actuators can be associated with one another such that extracted motor commands can be interpreted by the control software and translated into instructions to which the actuator can respond. When such instructions are generated, they can be transmitted to the one or more actuators, which respond with a movement. Transmission from a client computer to an actuator can be via a hardline or via telemetry or other wireless link. Summarily, when a client computer receives extracted motor commands, it performs any required processing of the signal and relays the signal to an actuator, which responds with a movement. The movement will correlate with the intended movement encoded by the brain-derived neural signal data. Although FIG. 1A depicts a skeletal robot arm, the term "actuator" is intended to encompass all forms of actuators, including prosthetics. Actuators suitable for use in the present invention will comprise sensory feedback circuitry and/or machinery.

When an actuator interacts with an object, the robot will gather sensory information regarding the object with which it is interacting. For example, a component of an actuator trajectory consistent with extracted neural command data can comprise the movement of grasping an object. When an actuator performs the movement, it will grasp the object.

Sensory feedback circuitry and/or machinery disposed on actuator then acquires information regarding the object, such as tactile information. The acquired sensory feedback information is then processed and transmitted back to the subject. The process of transmitting sensory feedback to the subject is generally denoted 90 in FIG. 1.

Sensory feedback information can be imparted to a subject in a variety of manners. For example, a physical stimulus can be imparted to the body of a subject. Alternatively, sensory feedback information can be processed and transmitted as electrical signals directly or indirectly to the brain of a subject.

An advantage of the closed loop brain-machine interface is its ability to translate neural signals into actuator movement in real time. That is, there is essentially no observable delay between the gathering of neural signal data and the movement of an actuator. Additionally, once implanted, the present invention can operate continuously or, at the subject's discretion, discontinuously.

The above discussion of the embodiment of the present invention disclosed in FIG. 1A and the general operation of the present invention is supplemented by the following sections and the remainder of the specification.

III.A. Implantation of Electrodes

Conventional neurosurgical techniques can be employed to implant microwire electrode arrays in appropriate brain areas. In one embodiment, a series of small craniotomies (preferably about 2–5 $mm^2$) through the skull of a patient can be used to gain access to the cortical areas of interest. Another series of smaller holes (preferably about 0.5 $mm^2$) can also be drilled in the patient's skull for placement of metal screws, which can be employed to provide support for the microwire arrays and a common reference for chronic electrophysiological recordings. Microelectrode arrays can be placed stereotaxically, and fixed in position using dental acrylic. Throughout the implantation process, single units are recorded and the location of their receptive field is qualitatively characterized until the arrays are positioned in the structure of interest. Intracranial microstimulation can also be employed to locate the arm and hand regions of the different motor cortical areas that will receive implants.

When these electrode arrays and devices are to be implanted in humans, functional MRI (fMRI) technology can first be used to identify those brain regions that the patient still has under voluntary control, thus allowing precise, functional placement of the implants and the recording electrodes.

III.B. Acquisition of Brain-Derived Neural Signals

Brain-derived neural signals can be collected by microwire electrodes configured as an array or as a bundle. Brain-derived neural signals are generally electrical in nature and can be carried by a conductive material. Microwire electrodes gather electrical neural signals from the region or regions in which the electrodes are implanted. The electrical signals are transmitted through the electrodes to one or more implanted neurochips.

The one or more implanted neurochips can be fabricated to accomplish a variety of goals. Preferably, a neurochip is adapted to receive the neural signals and to filter and amplify the signals. The precise nature of the signal filtration can vary with the desire of the neurosurgeon implanting a neurochip. Similarly, the degree to which the signals are amplified can vary with the needs of the individual implanting the neurochip or chips. Unique physiological aspects of the patient in whom the neurochip or chips are being implanted can also be taking into account.

An implanted neurochip or collection of neurochips essentially serves as the first stage of the signal processing treatment. After filtering and amplification, the neurochip can multiplex the neural signals and transmit the signals to a data acquisition unit. The mechanism of the transmission can be via a cable or by telemetry or other wireless manner. Preferably, a neurochip is adapted to transmit the signals via telemetry because, when this manner of transmission is employed, the skull and scalp of the patient can be fully closed, permitting an implanted neurochip and electrodes to operate without the need for the patient to be physically associated with the data acquisition unit. This approach also minimizes the chances of infection and other undesired conditions. Aluminum trioxide may be used as an insulating neurochip sealer.

A data acquisition unit is adapted to receive neural signal data from the implanted neurochip or neurochips and perform any desired preliminary processing of the signal. A preferable data acquisition unit comprises an MNAP (available from Plexon Inc. of Dallas, Tex.), which operates to receive neural signal data and distinguish signals between single neurons. A data acquisition unit can function not only as a collector for gathered neural signal data, but also as a preliminary signal processing station. Preliminary processing can comprise identifying the region of a subject's brain from which a neural signal originates. Additional preliminary processing can comprise, among other operations, identifying a quality of an action potential, determining the timing of an action potential and calculating the number of action potentials per second (i.e., a firing rate) of each recorded neuron.

III.C. Processing of Brain-derived Neural Signals

Processing of brain-derived neural signals can occur, preliminarily, when a data processing unit receives the raw stream of action potentials. Preferably, the majority of signal processing occurs when the gathered neural signals arrive at a processing computer. When the signals arrive at a processing computer, the signals relating to one or more motor command are identified and motor command and/or trajectory data is extracted from the neural signals.

III.C.1. Extraction of Motor Commands

When brain-derived motor command signals are received by a processing computer, neural signals relating to motor commands are extracted from the collection of gathered neural signal data. Since a closed loop brain-machine interface that is implanted in a human is preferably in continuous operation following implantation, neural signals will be continuously gathered and relayed to a data processing unit. Many of the gathered neural signals will not be related to motor commands, and therefore, it is desirable to separate signals unrelated to motor commands from signals related to motor commands. Identification algorithms running on a processing computer can perform this identification process. However, identification of signals related to motor commands can be performed at any point before an extraction of motor command or trajectory prediction data is performed. Alternatively, identification of these sequences can be performed as a component of the motor command or trajectory prediction deconvolution. Subsequent to identification of motor command-related signals, a deconvolution is performed to extract a trajectory prediction from the motor command-related signals.

III.C.2. Deconvolution of Motor Command and Trajectory Prediction Data

A real-time deconvolution analysis to identify a trajectory prediction comprises an adaptive routine, which permits repeated unsupervised fitting of both linear and ANN models throughout a recording session. Thus, the first minute of data in each recordings session can be used to compute the first version of both linear and ANN models using two separate computers. The resulting fitted models can then be sent back to a server and/or data acquisition unit where the actuator position is instantaneously and continuously predicted using neuronal ensemble firing data acquired in real-time. Both models can be repeatedly calculated as fast as possible, using the most recent available data. Dual 800 MHz PC-compatible computers can be employed to perform a fitting. All these calculations can be performed by software designed for a suitable platform, such as MATLAB®, available from The MathWorks of Natick, Mass.

One result of a deconvolution analysis of neural signal data is the identification of a trajectory through which a subject desires a body appendage to travel. For example, a trajectory might be the path in space through which a patient desires his or her arm to move when the impulse to raise the arm is formed in the brain of the patient. Neural signals formed in certain regions of the patient's brain encode the motor commands associated with performing this motion. A deconvolution analysis of these neural signals results, in part, in a trajectory through which the patient is directing his or her arm to travel.

III. D. Transmission of Actuator Position

As the data processed by a linear or ANN-based algorithm become available, the data (which can comprise impulses to move an actuator to a given three-dimensional coordinate in space) can be broadcasted via TCP/IP-adapted server to one or more computer clients. These clients can be responsible for controlling the 3-D movements of the actuator, such as a robotic arm (e.g., PHANTOM™, available from SensAble Technologies of Woburn, Mass.), or one or more actuators that mimic one or more appendages of a patient.

By employing this approach, one or more remote devices can be controlled directly using brain-derived signals. In this application, as an actuator moves, a signal describing its position in space is recorded on each client machine. Thus, one can measure the accuracy with which both local and remote actuator movements match the trajectory signals generated by one or more models (i.e., a linear model and an ANN model).

Alternatively, as the results from the one or more models become available, they can be broadcasted via telemetry or via a cable or other hardwire link to an actuator. Such an actuator is, therefore, adapted to receive the results.

III.E. Movement of an Actuator

In one embodiment, an actuator of the present invention serves as an analog for an appendage that a patient has lost or that the patient has lost motor control over. That is, the actuator effectively takes the place of the lost or paralyzed appendage. In this embodiment, therefore, an actuator preferably facilitates the overall same range of motion as the appendage for which the appendage is an analog. Additionally, it is preferable that the actuator comprises the same joint structure and motion range associated with the analogous joint in the patient's body. As a consequence, it is preferable that an actuator is capable of moving only through the range of motions the analogous structure in the patient is capable of moving through.

A goal of the closed loop brain-machine interface is to control the movement of an actuator via neural signals originating in the nervous system of a patient. The movement of an actuator of the present invention can be controlled by neural signals derived from the brain of a patient. That is, the three-dimensional coordinate position of an actuator at any given moment in time corresponds to the intended position of the actuator as determined by deconvolution of brain-derived neural signals.

In operation, the actuator receives the deconvoluted neural signals and moves to the three-dimensional position in space corresponding to the position encoded by the neural signals. Typically, the movement of an actuator from a first position to a second position is a trajectory comprising a plurality of intermediate points in space. Thus, the movement of an actuator from a first position to a second position can be accomplished by performing a series of smaller movements, each of which is encoded by one or more brain-derived neural signals.

Since the closed loop brain-machine interface operates in real time, the motion of an actuator will appear to observers, including the patient, to be a smooth motion. Although the overall trajectory of an actuator might comprise a series of smaller composite motions, these smaller motions will flow together apparently seamlessly, thereby creating a smooth motion along a trajectory by an actuator. This smooth motion is one consequence of the real time operation of the closed loop brain-machine interface.

III.F. Feedback from the Actuator to a Patient

In one aspect of the present invention, sensory feedback is acquired by the actuator and transmitted back to a patient. The actuator is therefore adapted to acquire sensory feedback and transmit acquired feedback to the patient. Sensory feedback can be acquired contemporaneously or subsequent to the motion of the actuator itself. Suitable sensory feedback circuitry and/or associated structures are, therefore, preferably associated with the actuator itself.

The nature of the sensory feedback mechanism of the actuator will, in part, determine the nature of the sensory feedback transmitted to the patient in or on which the closed loop brain-machine interface is disposed. A variety of sensory feedback mechanisms can be employed by an actuator of the present invention. For example, the actuator can transmit sensory information directly to the brain of a patient. Alternatively, an actuator can provide a physical stimulation to the body of a patient. Additionally, simple visual feedback describing the motion of the actuator can help the subject in controlling the displacement of the actuator.

In operation, sensory feedback, such as size, weight, shape, hardness, temperature or texture, can be acquired when an actuator interacts with a physical object. This interaction can come at the end of a trajectory followed by an actuator, such as when an actuator grasps an object. Alternatively, an interaction can come inadvertently, or by command, as an actuator is following a trajectory deconvoluted from a plurality of brain-derived neural signals.

When an actuator interacts with a physical object, it acquires sensory feedback about the object. This feedback can then be processed by feedback processing circuitry disposed on the actuator itself or at a location remote from the actuator. The feedback processing circuitry can function to translate tactile information into a signal that can be perceived by a patient. This signal can take the form of a physical stimulation, electrical signals transmitted to the nervous system of a patient or any other form capable of imparting sensory information to a patient.

III.G. Calibrating the Closed Loop Brain-Machine Interface

A valuable application of the present invention is to restore movement and feeling to a patient who has lost motor control over one or more of his or her limbs. Often a spinal cord injury or a congenital or degenerative condition can result in a loss of control over a patient's limbs, leading to a decreased quality of life. The present invention solves this and other problems by disclosing apparatuses and methods that a patient can employ to regain a degree of freedom of movement.

In an aspect of the present invention, the closed loop brain-machine interface can be calibrated or "trained" by a patient to recognize the patient's brain activity associated with a given motion. That is, the present invention can heuristically "learn" to identify the brain activity associated with a desired movement, such as raising of a patient's arm, side to side motion of a patient's arm or the range of three-dimensional spatial motion of a patient's arm. The closed loop brain-machine interface can be trained to recognize a similar range of movements for any appendage. By training the closed loop brain-machine interface to recognize the brain activity associated with a range of motion, a patient's desire to move an appendage in a given direction or pattern can be translated into motion by an actuator. Therefore, it is preferable to "train" or calibrate the brain-derived signals of a patient with a given motion.

A series of steps that can be followed by a patient (although a human patient is referred to in this example, animals can also be patients, as disclosed in the Laboratory Examples) in setting up, calibrating, and using the closed loop brain-machine interface can be as follows. The control of an artificial limb, or of stimulation of paralyzed muscles of the limb, to produce a particular motion can be used as a particular example to illustrate one training protocol. It is assumed in this description that two prior conditions have been met. First, the electrodes have been implanted in brain regions that have been shown with functional imaging procedures to be under the patient's voluntary control; i.e., which are "activatable" by the subject when desired. It is preferable that the electrodes be implanted in a brain region that is normally activated when the patient attempts one or more of the particular movements that the artificial limb will be asked to generate, though this is not an absolutely necessary requirement. Second, the channel gains and other parameters will have already be set and optimized after the implantation of the electrodes and other hardware components of the closed loop brain-machine interface. In order to calibrate the closed loop brain-machine interface, each day or at regular intervals following an implantation procedure, the patient can perform the following calibration routine, or a routine similar to that described hereinbelow.

First, the patient learns to use a particular, monitored biological signal to turn on a system calibration computer. A system calibration computer can be employed to record and store the various brain signals associated with a given movement and can direct the training procedure. If a patient has no control over his or her arms or legs, eye movements can be employed to turn on the calibration computer and control the operation of the computer. If eye movements are intact, signals could be a patterned sequence of eye blinks, sensed by a small monitoring device, which would not occur normally. If control of certain neck or facial muscles remains, their electromyographic activity could be used in the same coded way. For a totally paralyzed patient, the signal could be a particular time code of brain activity, generated voluntarily by the patient, but unlike a signal that would occur during normal operation of the external device. A similar set of signals can be used to turn the calibration system off, or later, to turn the device to be controlled on or off, after the neural control system has been calibrated.

Next, with the assistance of another person, or again using a coded sequence of biological signals, the patient selects a particular movement for calibration from a predetermined list. When a patient is calibrating a prosthetic arm, the list can comprise the following non-limiting list of options: alternate flexion and extension of the elbow; flexion-extension of the wrist; movements about the shoulder; grasping and releasing of an object; reaching to different points in space; or some combination of these.

When the patient gives a "ready" signal, the selected movement is displayed on a video monitor, and can be simulated by animation or a video record of a model performing an actual movement. The model movement is performed at a slow to moderate speed and, during its performance, the patient "tracks" the observed movement by attempting to move his/her own limb in exactly the same manner and at the same speed, even though actual motion might not result. A goal of this process is to generate signals in the patient's brain associated with that motion, which can be identified and employed in the closed loop brain-machine interface. Any number of repetitions of the motion can be performed, however the calibration will be more accurate if a higher repetition rate is chosen. During these repetitions, the system cross correlates the neural signals with the model movement(s) or some selected parameter of that movement (e.g., position, velocity, acceleration); and, on the basis of the average of these correlations over the repetitions, determines which subset of neural channels was most highly correlated with the model movement and its parameters. A calibration procedure can involve a variable number of repetitions for a given motion, and a collection of motions for which a number of repetitions can be performed.

The activity on the selected subset channels can then be routed to one or more DSPs, processed through motor signal extraction algorithms and passed to algorithms that control the components of the external device and thereby produce a movement like the movement performed by the model. Another set of repetitions can then performed and, following suitable signal processing and correlation, the appropriate "map" of these selected neural inputs can then be stored as a record of parameter values for the model movement.

The patient performs this same procedure for the next movement in the set and so on, until a complete calibration procedure has been performed. The calibration procedure can be performed daily or only at needed intervals, such as when the subject notices a diminution in control accuracy, with the optimal neural channels being reselected at each calibration procedure and mapped again onto the desired movement functions. Thus, this periodic calibration procedure adapts to or allows compensation for changing neural signal parameters, and it ensures the optimal selection of those channels that are still useful at any time for device control.

Additionally, the subject's own brain can also adapt to changing signal properties and the challenges that these changes impose on device control. That is, if the subject can voluntarily activate the brain region from which signals are monitored and can vary these signal levels, then (s)he can learn to modulate these activation levels so that the external device can still be manipulated, even if there is drift or other unknown changes in the activity of the recorded neural channels.

Summarizing, in a general calibration procedure can be employed to "train" the closed loop brain-machine interface of the present invention to recognize and correlate brain-derived signals with physical movement of an actuator. In a representative procedure, a paralyzed patient observes a set of simulated appendage movements (or other activities) on a computer screen, and attempts to "track" or emulate these same movements with attempted movements of his or her own paralyzed appendage. During the emulation process, the activity on each neural channel can be cross-correlated with selected parameters of the simulated motion point rotation, position of the appendage in space, speed of movement, and other parameters, to determine the movement parameter with which it is most highly correlated. The activity of this most correlated channel can then be "routed" or "distributed" to the circuit which controls the device component or movement parameter with which it is most highly correlated. Since this calibration procedure can be performed readily by the subject or patient on a periodic basis, the optimal neural channels for control of the external device can be reselected and redistributed each time, thus providing a continuing adaptation to changing neural signals, regardless of the cause of these changes.

Many modifications and variations of the training and calibration protocols of the present invention are possible will be known to those of skill in the art upon consideration of the present disclosure, without departing from the spirit and the scope of the invention disclosed herein.

IV. Components of the Closed Loop Brain-machine Interface

Broadly, the closed loop brain-machine interface comprises four major components: a mechanism of acquiring signals from the brain of a patient; a mechanism of extracting motor commands from the acquired signals; a mechanism for translating motor commands into movement instructions directing the movement of an actuator; and a mechanism for sending sensory feedback information from the actuator back to the brain of a patient, such that the patient "feels" the actuator's interaction with its environment. The four major components are identified merely for clarity of discussing the present invention; the division of the present invention into component parts is purely a matter of convenience and is not intended to limit the present invention in any way.

IV.A. Electrodes for Motor Command Signal Acquisition

Motor command signal data employed in the present invention can be acquired directly from the brain of a patient. Motor command signal data can take a range of forms, however the present invention preferably employs electrical signals generated by a patient's brain. Electrodes can detect electrical activity occurring in a patient's brain.

In one aspect of the present invention, measurements of extracellular electrical activity are acquired. Measurements of extracellular electrical activity are measurements of the electric activity of populations of single neurons in an area or region of the brain or other nervous system structure. The extracellular electrical activity, which can be acquired at a variety of locations within the brain and nervous system of a patient, thus represents a sum of the electrical activity generated by a plurality of neurons disposed in the area surrounding the extracellular electrical activity measuring device.

By way of example, when an individual monitors extracellular electrical activity of the primary motor cortex of a patient's brain, for example, what is detected is the activity of individual neurons in the primary motor cortex, which have spread through the tissues. These nerve cells can be characterized as point dipoles. In other words, each cell has a current source where positive charge moves outwardly across its membrane and a current sink where the same amount of positive charge moves inwardly at each instant. Thus, the flow of current across each cell establishes electric activity in the neural tissue that is similar to the electrostatic field potential of a pair of point charges, one positive at the location of the current source and one negative at the current sink. In the context of the present invention, it is preferable to record the individual action potentials from as many neurons in a given brain motor area as possible. Thus, the best "raw" signal can be found by recording a plurality of these action potentials.

In one aspect of the closed loop brain-machine interface, real-time measurements of motor commands, which take the form of electrical signals, are acquired from various points in the brain or neural tissue of a subject. The acquisition of real-time measurements of electrical brain signals describing motor commands permits the real-time evaluation and analysis of motor command data. Thus, real-time data acquisition and analysis enables an ongoing evaluation of data in the same time frame as the data is acquired. When real-time data acquisition and analysis is performed, there is no delay between data acquisition and the ability to access, analyze and evaluate the acquired data.

As disclosed hereinbelow, the present invention makes possible a variety of real-time brain-derived motor command data acquisition methods. For example, the present invention discloses employing microwire electrode arrays and microwire electrode bundles to acquire brain-derived motor command data in real time. Microwire arrays and bundles are preferred for the acquisition of data, however, any suitable electrode can be employed, such as electrodes disposed on or under the surface of a patient's skin.

In the present invention, brain-derived motor command data, which take the form of electric signals, are conducted by electrodes through the electrodes to a neurochip, where the signals are filtered, amplified and multiplexed, and then to a data acquisition unit where the signals are stored and analyzed. Therefore, suitable electrodes for practicing the present invention will be conductive and, if the electrodes are to be implanted in the tissue of subject, biocompatible with a body and tissues of the subject. As disclosed hereinbelow, however, electrodes need not be implanted and can be secured on or under the skin of a subject. These electrodes will also comprise a conductive material. TEFLON® coated stainless steel or tungsten wires are particularly preferred electrodes.

IV.A.1. Preparation of Microwire Electrodes

Microwire electrodes can be employed in the present invention to acquire brain-derived signals related to motor commands. Such signals can take the form of electrical activity in the brain or neural tissue of a subject. Preferably, the microwire electrodes are arranged in arrays or bundles. In a preferred embodiment, a microwire array comprises a plurality of stainless steel microwires. Preferably, the microwires are dimensioned so as to make them suitable for implantation with a minimum of tissue disruption. Suitable microwires can be manufactured using standard wirepulling techniques or can be purchased commercially from a vendor (e.g., NBLabs of Denison, Tex.). Suitable microwires electrodes can be formed of a conductive material, such as stainless steel or other conductive material.

When microwire electrodes are to be implanted in the brain tissue of a subject, it is preferable to coat the exterior of the microwire electrodes with polytetrafluoroethylene (marketed by DuPont, Inc. of Wilmington, Del. under the trade name TEFLON®) or other insulating material. TEFLON® coating the microwire electrodes offers a degree of insulation for the microwires, which not only isolates the surrounding tissue from the microwire material but also permits a more spatially-focused determination of a measurement from a large population of single neurons. Coating the microwires offers the additional advantage that motor command data can be acquired exclusively at that area of the microwire that is not coated (i.e. the non-insulated cross sectional area at the end of the implanted end of the microwire electrode).

IV.A.2. Microwire Electrode Arrays

Microwire electrode arrays, a preferred structure for acquiring brain-derived motor command data in the present invention, can be formed generally as follows. Initially, a plurality of suitable microwires, such as those disclosed above in section IV.A.1., are provided. Microwire electrodes will have first and second ends: the first end is defined as the end of the electrode that, when emplaced, contacts the brain or neural tissue, while the second end of the electrode ends at a terminus such as an interface with a head stage, signal amplifier neurochip or other equipment.

A microwire electrode array preferably comprises TEFLON® coated stainless steel microwires and can be chronically implanted in different cortical areas involved in the generation of motor commands. Thus, a microwire electrode array preferably comprises a plurality of microwire electrodes having free and flexible first ends, while having second ends oriented in a particular spatial arrangement. An advantage of the orientation of the second ends of the microwire electrode is that trains of action potentials can be recorded in a channel-specific fashion, due to the ability to easily correlate the position of a microwire electrode in situ with the position of the second end of the microwire electrode in the terminus.

Preferably, the micowires of a microwire array are 16–48 or 25–50 μm in diameter and the microwires are distributed in 2–6 rows of eight to sixteen wires each. The distance between the microwire rows preferably varies from 0.5 to 1 mm and the distance between pairs of microwires in a row preferably varies from about 300 to 500 μm. Overall, a microwire array itself can be packed in a very small configuration, so that many such arrays can be implanted in the same subject.

In a preferred method of making a microwire electrode array, the microwires are first glued together using epoxy. A coating of polyethylene glycol (PEG) can be employed to provide further support to the matrix, and the PEG will dissolve away as the array is implanted in a patient's brain. In rats and monkeys, the co-inventors have seen no evidence of any damage, irritation or gliosis beyond that expected due to the implant itself. Gas or chemical sterilization can be employed for the implantation of microwire arrays.

It is preferable that each microwire electrode be monitored on its own channel, so as to avoid a global average of data acquired by all of the microwire electrodes. By monitoring each electrode on its own channel, it is possible to simultaneously monitor a variety of regions of tissue in a single subject's brain and thus more efficiently acquire trains of action potentials that encode brain-derived motor command data.

IV.A.3. Microwire Electrode Bundles

The closed loop brain-machine interface can also employ microwire electrodes arranged as a bundle, as an alternative to the microwire electrode array disclosed in section IV.A.2. above, for acquiring brain-derived motor command data. When a microwire electrode bundle is employed, the microwires preferably are manufactured of a conductive material, such as stainless steel or tungsten, and are at least partially TEFLON® coated.

The microwire electrodes of a bundle will also have first and second ends. The first end or each electrode member of the bundle contacts the tissue, while the second end interfaces with a head stage, signal amplifier or other piece of equipment. However, unlike the electrodes of an array, the individual electrodes of a microwire electrode bundle are secured in close proximity to one another and it is presumed that all members of the bundle can be implanted in the same general location in a subject's brain tissue, the bundle being considered a single unit for implantation purposes. Microwire bundles are preferred for implantation in deep subcortical motor structures, such as the basal ganglia and the motor thalamus.

A microwire electrode bundle comprises a plurality of microwire electrodes. Each individual member of the bundle can, but need not be, of a different length. When a microwire bundle comprising electrodes of different lengths is implanted in brain or other tissue, the each electrode of the bundle is generally localized to a single region of tissue, however the different lengths of each microwire electrode facilitates acquisition of data at a different tissue depth, effectively providing a depth profile of measurements from a large population of single neurons. Comparing microwire arrays and bundles, the arrays permit data acquisition from multiple sites, while the bundles typically permit data acquisition from multiple depths of the same site.

Like the microwire electrode array, it is preferable that each microwire electrode of a microwire bundle be monitored as a separate channel. This practice facilitates the monitoring of brain tissue at different depths on and electrode-by-electrode basis, as opposed to monitoring the brain tissue as a global average of measurements.

IV.A.4. Less Invasive Electrodes

The above discussion has focused primarily on the use of microwire arrays and microwire bundles, each of which is preferably implanted directly in the brain or other nervous tissue of a subject, the present invention is not limited to these methods of acquiring brain-derived motor command data; less-invasive and non-invasive methods and apparatuses can also be employed in the present invention in order to acquire motor command data from the electrical activity present in a patient's brain or nervous system.

It is known in the field of neurology that it is possible to detect EEG biopotentials on the outer surface of the head or brainwaves that demonstrate continuous electrical activity in the brain. The intensities of the brain waves or EEG on the surface of the scalp generally range from zero to 300 microvolts, and their frequencies range from once every few seconds to 50 or more per second. Much of the time, the brain waves are irregular, and no general pattern can be discerned in the EEG. At other times, however, distinct patterns are present. Activities within the various EEG spectrums have been correlated to states of sleep, relaxation, active thought, etc. Depending on the nature of the activity of interest, it is known to detect EEG waves at different areas on the scalp as a function of the part of the brain of interest.

A representative non-invasive approach to the acquisition of brain-derived motor command data, then, can involve placing suitable electrodes on the scalp or other exterior position of a subject's skin proximate to the organ, structure or region from which measurements from a large population of single neurons is to be acquired. Suitable electrodes can be fixed in place, for example, by employing a temporary adhesive. It is important, however, that once placed an electrode it is not free to move, since movement might decrease the quality of motor command data acquired from the electrode. Suitable electrodes can be manufactured or purchased commercially.

Alternatively, a less invasive approach can be taken with respect to electrode positioning and emplacement. For example, in lieu of placing electrodes directly in the tissue of a subject's brain, electrodes, including microwire electrodes, can be placed subdurally, thereby circumventing the need to insert electrodes into the brain itself. When electrodes are placed subdurally, it is preferable that the electrodes be positioned in areas known or suspected of being involved in the generation of motor commands. When placing electrodes subdurally, at least one craniotomy will still be performed, although in this method there is no requirement that the electrodes be placed directly in contact with cortex or other brain or neural tissue.

A less invasive alternative to placing electrodes for acquiring brain-derived neural signal data directly in contact with brain or neural tissue is the use of sub-skin emplacement of electrodes. In this approach, electrodes can be implanted under the skin of a subject, for example under the scalp of a subject, in the proximity of regions of the subject's brain or other neural tissue known or suspected to be involved in the generation of motor commands. This approach obviates the need for performing a craniotomy. The small dimensions of the microwires also make this form of emplacement an attractive option.

A variety of types of electrodes can be employed in the disclosed less-invasive and non-invasive methods. For example, microwire electrodes can be employed in the subdural and sub-skin approaches. Microwire electrodes can also be employed in non-invasive approaches as well. However, the more spatially distant an electrode is located from the region it is to monitor, the more sensitive the electrode needs to be. Restating, in non-invasive approaches it is preferable to employ a more sensitive electrode than those electrodes that are to be placed directly in contact with tissue. Preferred electrodes for use in non-invasive approaches can be electrodes of larger dimensions than a microwire electrode, or of greater sensitivity. Additionally, signal amplifiers can help to compensate for any observed low signal amplitudes.

IV.B. Hardware and Software for Processing Neural Signals

In one aspect of an embodiment of the present invention, one or more microchips are employed for various purposes, such as signal amplification, signal filtering, multiplexing, analog-to-digital conversion and radio transmission of signals to external receivers. For example, preamplification of multiple channels of neural data, multiplexing of neural data from multiple channels into a single data stream, and radio transmission out of the body of a subject can be accomplished by a microchip, or a plurality of microchips, coupled to a microwire electrode array. The microchip, as well as the array itself, is preferably adapted to be implanted in the neural tissue of a patient.

In another aspect of an embodiment of the present invention, external receivers and demultiplexers can be employed for allowing the exteriorized data stream (i.e. data transmitted outside the body of a patient) to be detected and reseparated into separate neural data channels, which can then be individually selected and mathematically transformed for control of one or more exterior devices (e.g. an actuator such as an arm prosthesis) or device components (e.g., separate parts of the actuator or arm prosthesis).

IV.B.1. Implantable Neurochip

The closed loop brain-machine interface relies, in part, on a specially designed implantable neurochip. The implantable neurochip interfaces with, at least, the electrodes that acquire extracellular electrical signals associated with motor commands and a Many Neuron Acquisition Processor (MNAP), such as those available commercially from Plexon Inc. of Dallas Texas. Although the implantable neurochip can function in a range of capacities, the neurochip will function at least to amplify, filter and telemeter data to a MNAP. The neurochip can also be designed to incorporate a multiplexer, which can multiplex acquired signals into a serial data stream for transmission. By employing current chip technology, the neurochip can be fashioned with small dimensions, thereby making it suitable for implantation in the body of a subject. Aluminum trioxide may be used as an insulating neurochip sealer. Effectively, the neurochip can serve as a head stage for gathering and transmitting data acquired from the electrodes.

In one aspect of an implantable neurochip of the present invention, the neurochip comprises architecture and circuitry that can receive neural data acquired by electrodes and transmitted through the electrodes to the neurochip. The neurochip then amplifies the signals to a desired level via a preamplifer. Additionally, the signals are filtered by the neurochip and transmitted to a MNAP. The signals can also be fed into an on-chip multiplexer, which multiplexes these signals into a serial data stream for transmission.

Amplified signals can then undergo a filtration process. For example, a filtering process that can be employed can comprise a 500 Hz to 5 KHz band filter. Other filtering processes can be employed and can be dictated by the volume and character of signals. Such signal filtration processes will be apparent to those of skill in the art upon consideration of the present disclosure. An implantable neurochip can also be configured to amplify the signals before they are filtered.

Transmission of the signals to the MNAP can be achieved in a variety of ways, although a preferred method of transmission of signals is via wireless circuitry and more preferably via radio telemetry. In this embodiment, signals that have been treated by the neurochip are transmitted by radio waves to the MNAP, which can be disposed outside of the body of a subject in which the neurochip is implanted. In a laboratory setting, it can be desirable to transmit signals from the neurochip to a MNAP via a cable or other hard line and the neurochip can be designed in contemplation of this possibility, and the present invention contemplates this possibility.

Preferably a neurochip is designed to amplify, filter, multiplex perform analog-to-digital conversion operations and transmit signal data in a channel-by-channel fashion. This approach permits signals acquired from different locations in the brain of a subject to be treated individually and indeed data from single neurons can be acquired as such. Thus, it is preferable that each electrode be treated as a separate independent channel. This can lead to not only a more effective understanding of complex motions (such as the range of motions available to an arm or other appendage) but can lead to more accurate interpretation of the signal data acquired by the electrodes. When a channel-by-channel treatment of the data is desired, the amplifier and filter circuitry can comprise multichannel amplifiers and multichannel filtration circuitry.

IV.B.2. Multichanel Many Neuron Acquisition Processor (MNAP)

Simultaneous recording of the extracellular electrical activity of large samples of single neurons is also facilitated, in part, by the use of a multi-channel Many Neuron Acquisition Processor (MNAP), such as those available from Plexon Inc. of Dallas, Tex.

Broadly, an MNAP comprises signal input circuitry, which can take the form of a circuit board, can comprise one or more signal amplifiers, signal conditioning circuitry, although, this can be integrated into the circuitry of the neurochip, digital signal processing circuitry, hardware running one or more action potential detection algorithms, hardware and/or one or more algorithms adapted to analyze and/or process action potential timing data, one or more timing boards, an output board and a host link subsystem. It is noted, however, that these various aspects of a MNAP can be integrated one to another, and therefore the disclosed components of a MNAP should be understood to be a general list, and not a checklist of components required to be disposed in a MNAP of the present invention.

The MNAP signal input circuitry is adapted to receive signals from the neurochip. Thus, if the neurochip is adapted to transmit data by radio telemetry, the MNAP signal input circuitry should be adapted to receive data in that form. Alternatively, if signals are to be transmitted to the MNAP via cable link, the MNAP signal input circuitry should be adapted to receive data transmitted in that form.

Signal amplifier and signal conditioning circuitry can also reside on the MNAP, although these components are preferably disposed on the neurochip. For example, programmable gain, filtering and A/D conversion for each channel can comprise the signal amplifier and signal conditioning circuitry. Additionally, signals can be filtered using a low cut-off and high cut-off filters. Additionally, a programmable gain multiplier can also form a component of a signal amplifier or signal conditioner of an MNAP.

The MNAP preferably comprises one or more timing boards. Timing boards can, among other tasks, provide global timing to signal input circuitry and to DSP boards, which are discussed further supra. A timing board can also monitor spike event signals and provide synchronization and control signals to the DSP boards. Timing boards are particularly useful in signal processing, although timing boards can also take a role in orderly signal acquisition.

A host link subsystem can also form a component of a MNAP. The host link subsystem can facilitate the transmission of processed signals to a host computer where the signals can be stored and visualized. Additionally, the host computer can be adapted to form permanent recordings of the signals relayed by the host link subsystem. Permanent recording of the signals can be achieved, for example, by storing the signals on CD.

In a preferred configuration, an MNAP allows simultaneous sampling from 128 microwire electrodes and discrimination of up to four individual action potentials per microwire, for a maximum of 512 recorded neurons. In this configuration, a neurochip is used as a head stage and can broadcast neuronal signals to a modified version of the MNAP via a telemetry link. The MNAP receives the signals that have been amplified and filtered by the neurochip and then routes these signals to one or more digital signal processing (DSP) boards, each of which contains one or more signal processors. In a preferred embodiment, each DSP board comprises four digital signal processors (DSP, MOTOROLA 5602) running at 40 MHz (instruction read at 20 MHz). Preferably, each DSP handles data from eight input channels and comprises 32K 24-bits of static random access memory (SRAM) and 4K 16-bit words of dual port SRAM memory. A timing board can be employed to distribute timing and synchronization signals to the entire MNAP. A DSP board can also provide inputs for sampling digital pulses generated from behavioral cages. A single host Pentium microcomputer (800 MHz, with 128 MBytes of RAM, and 40 Gbytes of disk space), running C++ software (SSCP software available from Plexon Inc. of Dallas, Tex.) on the WINDOWS® NT 4.0 operating system (available from Microsoft Corporation of Seattle, Wash.) can be employed to control the MNAP over a serial line.

IV.B.3. Signal Analysis Software

Various software programs can be employed to analyze signals acquired signals. Such software can be disposed on a DSP or on another electronic component. Signal analysis software can comprise, among other applications, a spike discrimination program, which can function to identify and isolate spike in an acquired signal profile. Spikes, as noted herein above, are generally indicative of a neuronal event, also known as an action potential.

Spike discrimination programs are preferably downloaded from a host computer to the one or more DSPs. In one embodiment, single spikes are discriminated by combining a modified version of a principal component algorithm, running in real-time, and one pair of time-voltage windows per unit (e.g., per microarray, microbundle, etc). The size and position of the time-voltage boxes are determined and set by an operator, so as to isolate the waveforms that belonged to a given unit.

In one version of this software, which is preferred for clinical application of the closed loop brain-machine interface, spike sorting can be carried out in an unsupervised way. During the recordings, the time of occurrence of each of the neuronal spikes, for all channels, is transferred to the hard disk of a host computer through a parallel bus (e.g., an MXI-Bus, available from National Instruments of Austin, Tex.), which is capable of transferring 2 MB of data per second. Digitized samples of the spike waveforms can be recorded periodically and stored off-line for analysis using a suitable visualization program. Suitable spike analysis programs can be written de novo in a computer language such as C++, or can be purchased commercially such as SpikeWorks, available from Plexon Inc. of Dallas, Tex.

Additional signal processing software can be employed in the present invention and can perform a variety of tasks. For example signal pretreatment software can be employed upstream from the spike selection software. Additional software can also be disposed on individual microchips or circuit boards, or it can be disposed on a component of a DSP.

Signal processing software can also be employed to identify the most appropriate application for each signal or group of signals. For example, if signals are derived from the "arm" area of the motor cortex, some of the signals can be related to shoulder movements, others can relate to movements about the elbow, some others can relate to movements about the wrist, and still others can relate to finger movements. In a paralyzed patient, the movements are "attempted," rather than actual, voluntary movements. If the signals are not derived from the motor cortex but are still under voluntary control by the patient and are to be used for control of arm prosthesis movements, signal processing software can also be employed to assist in making a determination as to which are the most appropriate signals for fine hand control, which are the most appropriate signals for upper arm control, and so forth. Recorded neural signals can also change over time, due to electrode "drift" within the brain tissue (so that the electrode moves away from some cells and closer to others), natural death of cells (50, 000–100,000 cells/day in the adult brain), or changes in the physiological properties of neuronal discharge in relation to movement which result from motor learning. Consequently, a signal processing software can be employed to adapt to, or partially compensate for, changes in recorded neural signals and their parameters over time, so that the same implanted electrode array remains applicable for control purposes for as long a time period as possible.

IV.C. Hardware and Software for Extracting of Motor Commands from Neural Signals Subsequent to the acquisition of motor command signals from the brain or neural tissue of a patient, the signals can be recorded and processed by a MNAP, as disclosed hereinabove in section IV.B.2. Following any desired processing of the raw signals themselves, motor commands can be extracted from the neural signals. That is, the actual patterns of neural activity coincident with a given motion are identified and extracted from the landscape of neural signals.

Broadly, extraction of motor commands from a landscape of neural signals can be achieved by employing a general approach of comparing the observed data with data known to be coincident with a motion. Thus, this component of the closed loop brain-machine interface is employed as a component of the real-time analysis of brain-derived signals that yields the motor commands used to define the x, y, and z coordinates of an actuator trajectory that mimics a patient's movement intention.

Off-line processing of the neuronal data can be employed initially to select the methods that offer the best prediction for actuator position, based on the concurrent activity of large networks of cortical neurons. Multivariate statistical methods, such as multiple linear regression and different multi-layer artificial neural networks, can be used to measure the ability of different populations of cortical neurons to contribute for the genesis of motor control signals. Once the off-line analysis is concluded, the selected algorithms are used to control an actuator, which can mimic the motion of a patient's appendage or appendages.

IV.C.1. Real-Time Analysis of Neural Data to Extract Motor Commands

In one aspect of the present invention, neural data is analyzed in real time. In the context of the brain-machine interface, this ability means real time data analysis can be translated into actuator motion virtually instantaneously. In other words, an advantage of the ability to analyze neural data in real time is that an actuator can respond to neural data effectively as soon as the neural data is acquired, analyzed and processed. When an actuator is disposed in or on the person of a patient, this means that as the patient forms the neural signals encoding a motion, those signals are translated into actuator motion, without any observable delay. Thus, to the patient, it appears that the actuator moves as the patient directs virtually at the same time as the neural signals encoding the motion are formed. Thus, when the present invention is situated in or on the person of a patient, real time processing of neural signals means an ongoing, continuous and uninterrupted analysis.

A goal of the real time analysis aspect of the present invention is the extraction of motor commands from the flow of impingent neural signal data. The extraction of motor commands is, therefore, an aspect of the real time analysis of neural signal data.

IV.C.2. Linear Model to Extract Motor Commands

Very accurate correlations of position and neural signals, which can be based on simultaneously recorded ensembles of cortical neurons, can be obtained by applying a linear model to multi-channel neural data. A suitable linear model can be based on an extension of the basic linear regression equation, y=ax+b, to the condition where the inputs (x) and outputs (y) are time series. In this case, significant coupling between inputs and outputs is typically not limited to observations that are simultaneous in time, but can exist over some range of time delay or lag between the signals. In the closed loop brain-machine interface, the inputs, X(t), are preferably a matrix with each column corresponding to the discharges of individual neurons, and each row representing one time bin. The outputs Y(t), are preferably a single vector of samples of the position in the 1-D case, and a matrix with three columns, one for each dimension, in the 3-D case. The linear relationship between the neuronal discharges in X(t), and actuator position in Y(t) is expressed as:

$$Y(t) = b + \sum_{u=-m}^{n} a(u)X(t-u) + \varepsilon(t)$$

where a and b are constants which are calculated to fit the model optimally. The term a(u) represents the weights required for fitting X(t) to Y(t) as a function of time lag u between inputs and the outputs. These weight functions are called impulse response functions. There is one impulse response function for each neuron in X(t) and dimension in Y(t) (i.e., with 50 neurons and 3-D movements, there are 150 impulse response functions). The term b represents the Y-intercept in the regression. Hence, b is a single number for 1-D movements, and a vector with 3 numbers, one for each dimension, for 3-D movements. The final term in the equation, $\varepsilon(t)$, represents the residual errors, i.e., any variation in Y(t) that cannot be explained by X(t).

In summary, in this model, the series in X(t) (i.e. neuronal firing in time) are convolved with the impulse response functions in a(u) so that the sum of these convolutions plus b approximates Y(t) (actuator trajectory). The limits of the time lag u (m and n in the above equation) are preferably set so that time lags for which statistically significant coupling exist between the signals in X(t) and Y(t) are included in the model. The desired values of m and n can be estimated by initially using large numbers, and then evaluating the impulse response functions statistically. As disclosed herein and in the Laboratory Examples hereinafter, these impulse response functions are significantly different from zero for time lags of up to one second in some cortical neurons.

In order to reduce the real-time computational load, and to be able to run the real-time model using regular computer workstations (e.g., a dual 800 MHz Pentium III, PC compatible microcomputer), the temporal resolution of the linear model can be reduced so that the number of discharges for each neuron is counted in 50–100 ms bins, corresponding to 10–20 Hz. To account for neuronal activity for lags of up to one second, 10–20 bins per neuron can be employed in the real-time linear model. The complete model for real-time actuator position is given by the following equation:

$$Y(t) = b + \sum_{u=0}^{9} a(u)X(t-u) + \varepsilon(t)$$

where the time variables t and u are in units of samples, i.e. 10 per second. Note that there are ten "copies" of X(t) used in the model, one for each integer value of u from 0 to 9. In other words, there are ten times as many inputs in this equation as there are neurons in X(t), each input corresponding to one appropriately time-shifted copy of each neuron in X(t). If a new matrix is created with all the copies of the neurons, X'(t), the equation becomes:

$$Y(t)=b+a'X'(t)+\varepsilon(t)$$

The weights, a', and the Y-intercept, b, can in this case be estimated directly in the time-domain using standard linear regression techniques. Empirically, we observed that real-time predictions of hand trajectory based on neural ensemble firing using this simplified model were only minimally inferior to the more complete model outlined in the previous section.

IV.C.3. Multi-layer Artificial Neural Network Model to Extract Motor Commands

A data structure similar to the data structure disclosed for the real-time linear model of section III.C.2. hereinabove can be employed when a real-time ANN is employed to derive motor commands from brain-derived signals. Different types of feed-forward ANNs can be employed successfully in the closed loop brain-machine interface. In this approach, data from the simultaneously recorded neurons constitute the input layer of the ANN. This input layer is connected to a hidden layer containing units defined by nonlinear output functions, so-called tan-sigmoid output function units. The hidden layer is connected to a final output layer whose units generated linear outputs to control the movements of an actuator. There is one output for an ANN employed to estimate position in 1-D, two outputs for 2-D movements and three outputs for 3-D movements. Several distinct algorithms can be employed to train these ANNs, including classical backpropagation with variable learning rates, resilient backpropagation, backpropagation using the Fletcher-Reeves and Polak-Ribiere variants of the conjugate gradient algorithm, the Fletcher-Reeves algorithm with Powell-Beale restarts, and the scaled conjugate gradient algorithm. Presently, the fastest fitting of the models and the best predictions can be obtained by employing one hidden layer with 15–20 units, and the Powell-Beale method. In addition, an early stopping rule is employed to avoid over-fitting of the data used for training the network and to improve predictions with new data. Trajectory and motor command data obtained from an ANN are comparable to those obtained by employing a linear algorithm.

IV.D. Movement of an Actuator

Presently, actuators and prostheses can be controlled through self-contained electronic controller means such as a microprocessor or dedicated circuitry. Sophisticated controllers comprising multiple input acceptance means for permitting the processing of input commands from various sources including potentiometer inputs, accelerometer inputs, touch inputs, and electronic sensory inputs such as force, pressure, or temperature sensor inputs, are known in the art. Controllers comprising multiple output deliverance means for permitting output proportional to input, i.e., an open loop operation, are also known in the art. However, a closed loop brain-machine interface, wherein signals derived from the brain of a patient are employed to direct the motion of an actuator and, subsequently, provide feedback to brain of the patient has been unattainable until the present disclosure.

A variety of actuators can be employed in the present invention. Generally, an actuator will be appropriate for the application to which the closed loop brain-machine interface is desired. For example, in one embodiment, a suitable actuator can be a prosthetic limb that can be disposed on, or associated with, the body of a patient. In this embodiment, the actuator is preferably designed to mimic the range of motion of the limb it is replacing. In another embodiment, the actuator can be a teleoperated robot arm that is adapted for work in a hostile environment such as space, a deep sea environment or even within a nuclear reactor. An actuator preferably has a range of motion permitting motion in three dimensions, however actuators adapted for motion in only one or two dimensions are also an aspect of the present invention.

A suitable actuator can be formed of any of a variety of materials, including metals, alloys and various plastics. The actuator will be adapted to receive signals derived from the brain of a patient. Thus, an actuator can comprise components and/or circuitry of a telemetry system or components and/or circuitry to facilitate transmission of brain-derived signals by hardwire. Since the present invention is a closed loop, the actuator will also comprise components and/or circuitry to detect and transmit sensory information from the actuator back to the nervous system of a patient. Broadly, then, the arrangement and components of a suitable actuator are governed by the application to which the closed loop brain-machine interface is put, with the caveat that the actuator is adapted to receive brain-derived signals, perform operations consistent with the brain-derived signals, and transmit sensory information back to the patient.

IV.D.1. Real-time Control of a Local Actuator

The closed loop brain-machine interface can be employed to control the motions of a local actuator. A local actuator can be an actuator that is disposed, for example, on or associated with the body of a patient or a short distance from the body of a patient. A local actuator can interact with the components and circuitry of the closed loop brain-machine interface via a wireless (i.e. telemetry) or cable link.

A local actuator is preferably adapted to respond to brain-derived signals in real time. In this embodiment, the actuator responds to brain-derived signals with one or more physical motions. That is, brain-derived signals are acquired, processed and transmitted at the fastest possible rate permitted by the components and circuitry of the brain-machine interface to the actuator. The actuator responds with one or more motions corresponding to the brain-derived signals without delay. Sensory feedback gathered by an actuator is then transmitted back to the patient, following any desired translation of sensory feedback into electrical or other signals. This process can be referred to as "real time" because the time required to perform the described series of operations is minimal (on the order of fractions of a second) and the correlation between the acquisition of brain-derived signals, actuator motion and receipt of sensory feedback is virtually instantaneous.

IV.D.2. Real-Time Control of a Remote Actuator

The closed loop brain-machine interface can be employed to control the motions of a remote actuator. A local actuator can be an actuator that is situated some distance from the body of a patient. Typically, the distance between the actuator and the body of the patient will be such that telemetry of information or transmission by a direct data link is not practical. In one embodiment, a remote actuator can interact with the components and circuitry of the closed loop brain-machine interface by means of a TCP/IP, telephonic, internet or other hardwire link.

Like a local actuator, a remote actuator is preferably adapted to respond to brain-derived signals in real time. In this embodiment, the actuator responds to brain-derived signals with one or more physical motions. That is, brain-derived signals are acquired, processed and transmitted at the fastest possible rate permitted by the components and circuitry of the brain-machine interface to the actuator. The actuator, in turn, responds with one or more motions corresponding to the brain-derived signals without delay. Sensory feedback gathered by an actuator is then transmitted back to the patient, following any desired translation of sensory feedback into electrical or other signals.

IV.D.3. An Actuator Adapted to Transmit Sensory Feedback to a Subject

One problem with existing actuators, such as prostheses, is a lack of direct tactile sensory feedback relating to the force being exerted by the device upon a manipulated object or upon a surface. For example, a user of a prosthetic arm or hand does not receive direct sensory feedback and thereby can control of the force being exerted upon manipulated objects with great difficulty. Similarly, a user of a lower limb prosthesis does not receive direct sensory feedback sufficient to permit, for example, control of the pressure force being exerted upon a contacted surface. A prosthetic limb device typically has a force capability much greater than a natural limb. A prosthesis user can generally learn, through training and repetition, and with reliance upon visual and auditory input, a degree of control of the contact pressure force being applied by the device. This degree of control is very imprecise, however, and often much more force than necessary can be applied. With respect to upper limb prostheses, handling of small, heavy, or fragile objects or performing precise tasks is often difficult. While perhaps less of a problem with respect to lower limb prostheses, improved control of the pressure force applied to surfaces while balancing to stand or lifting and lowering the prosthesis when changing positions or ambulating is desirable.

A potential approach to this problem with prosthetic hands was described by Goulding (Goulding, (1984) *Extended Physiological Taction, Design and Evaluation of a Sensory Feedback System for Myoelectric Control of a Terminal Device*, a thesis submitted to the faculty of the University of Utah, Department of Bioengineering. Goulding describes a pusher device, operated by a rack and pinion mechanism fixed to the shaft of a small DC motor with a gearhead transmission, was apparently utilized to apply a pushing force to a portion of a user's skin. The pushing force proportionally corresponded to a pressure force applied by a prosthetic hook on an object being gripped by the hook. The pressure force applied by the hook moment arm between the tip and base was sensed by a strain gage transducer and the converted signal was used to control the force applied by the pusher device.

Another approach is disclosed in U.S. Pat. No. 4,808,187 issued to Patterson et al. Patterson et al. disclose use of piezoelectric crystal pressure transducers positioned on a myoelectric prosthetic hand or forearm to sense the level of pressure force applied to a grasped object. The sensed pressure force is converted to a corresponding signal which eventually results in a proportional effect on the hydraulic pressure within a pressurizable cuff encircling a portion of the user's remnant limb. In particular, the signal corresponding to the sensed pressure force is received by control circuitry for processing and the processed signal instructs a hydraulic motor to proportionally expand or contract a hydraulic cylinder which in turn increases or decreases the hydraulic pressure within the cuff. The user thus receives direct tactile feedback in the form of increases and decreases in constriction of the cuff upon the remnant limb in response to increases and decreases in pressure force sensed by the transducers.

Another proposed solution to the problem of providing sensory feedback to a patient employing an actuator or prosthesis is the use of myoelectric devices. Externally powered myoelectric prosthetic devices have been developed which provide mode switching capability permitting a trained user to switch modes, i.e., degrees of freedom such as wrist pronation and supination, elbow flexion and extension, and hand closing and opening, with myoelectric signals from a particular muscle or muscle group control site. Thus, a skilled user can achieve the capability of smooth and rapid mode switching through selective flexure and contracture of specific muscles or muscle groups at a selected control site permitting a high level of function and control of the prosthetic device.

An example of a prosthetic limb incorporating a sophisticated controller which permits switching between multiple degrees of freedom and/or multiple functions with myoelectric input from one or more muscle or muscle groups is apparently found in U.S. Pat. No. 5,336,269 issued to Smits. Smits discloses a method and apparatus for switching between a plurality of degrees of freedom, e.g., wrist pronation and supination, elbow flexion and extension, and hand closing and opening. The apparatus comprises at least one surface electrode for picking up myoelectric signals of a muscle, circuitry for amplifying, full-wave rectifying and smoothing the myoelectric signals, an analog-to-digital converter for converting the received myoelectric signals to digital data, and a microcontroller having memory means and programming to operate the apparatus.

These proposed solutions to the problem of providing sensory feedback to a patient employing an actuator or prosthesis, however, do not permit the patient to actually control the prosthesis using brain-derived signals. The disclosed solutions do not comprise closed loop brain-machine interfaces. By contrast, the present invention provides a method and apparatus that enables a patient to employ brain-derived signals to control an actuator, which in turn, provides sensory feedback to the patient, thereby closing the sensory loop. An actuator of the present invention, therefore, is capable of providing sensory feedback to a patient.

V. Applications of the Closed Loop Brain-Machine Interface

The closed loop brain-machine interface apparatus and methods can be employed in a variety of different applications. For example, the present invention can be employed to enhance the quality of life of a patient by imparting a degree of control over an actuator. Additionally, the present invention can be advantageously employed as a way of interacting with non-natural or hazardous environments or materials.

In a preferred application of the closed loop brain machine interface, the present invention is employed to enhance the quality of life of a patient who has lost motor control over one or more appendages, Often such a patient has lost motor control as a result of paralysis, which can accompany a spinal cord injury and can result suddenly from a traumatic event. Alternatively, control can be gradually lost, as in the case of certain conditions, such as amyotrophic lateral sclerosis.

The present invention can also assist patients suffering from cerebral infarction, which is a severe cerebral dysfunction induced by cerebral ischemia or hypoxemia. With the increase of the aged population, the incidence of diseases or conditions, which can cause cerebral ischemia such as cerebral thrombosis and cerebral embolism, is increasing. Indeed, the number of patients suffering from cerebral infarction and having cerebral dysfunctions is continuously increasing. The present invention can return some, if not all, motor control a cerebral infraction patient has lost.

The present invention can also enhance the quality of life experienced by a patient who has lost an appendage entirely. For example, if a patient has lost an arm or leg, for example, as a result of an accident, the patient can be fitted with the closed loop brain-machine interface. This patient can then operate an actuator, which can have the full range of motion associated with a functional human arm, and, in effect, just as the patient would operate his or her own arm or leg.

Although a preferred application of the closed loop brain-machine interface comprises fitting a patient with the present invention in order to effectively "replace" an absent or paralyzed appendage or appendages, the present invention can also be employed in many other scenarios as well. For example, the present invention can be employed to operate one or more robot actuators, which are situated in a hostile environment, such as the deep sea, space and areas exposed to hazardous materials.

In another application of the present invention, a patient who has lost a degree of motor control by virtue of a spinal cord injury can be assisted. Often, a result of a spinal cord injury is the inability to transmit motor commands from the brain of a patient through to the structures that control muscle action. In effect, the spinal cord injury is a break in the chain between the patient's brain and his or her muscles. Sometimes, a patient is capable of forming the neural signals corresponding to a motor command and the patient's muscles are unaffected, yet the signals cannot reach the muscles and therefore the action encoded by the neural signals cannot be performed. The present invention can be employed to solve this problem.

An actuator of the present invention can comprise muscle stimulation circuitry and/or machinery. Representative muscle stimulation circuitry and/or machinery can comprise a device adapted to impart electrical stimulation to a muscle with which the device is associated. Thus, in this application of the present invention, the extracted motor commands can be relayed to an actuator adapted to electrically stimulate one or more muscles. The actuator, or an intermediary device, can then translate the extracted motor commands into one or more electrical stimuli, which are then imparted to the muscle. By applying the electrical stimuli to the muscles in certain strengths and at certain positions, the muscle will, in response, contract or release. In this application, the present invention is employed to effectively bypass the damaged region of the spinal cord and offer the patient the ability to control his or her motions via neural signals derived from the patient's brain.

VI. Conclusion

The closed loop brain-machine interface and the disclosed methods represent a significant advance in the fields of neurology and bioengineering. The closed loop brain-machine interface provides, for the first time, a system by which an actuator can be controlled directly by signals originating in the brain of a patient, and by which sensory feedback is transmitted from the actuator to the patient. The sensory feedback can be transmitted to the patient in a variety of ways, including physical stimulation and via direct microstimulation of the patient's nervous system. An implantable neurochip can be employed to assist in this process.

The closed loop brain-machine interface can greatly enhance the quality of life of patients who have lost a degree of motor control or who have lost the use of one or more given appendages. These patients can be fitted with the present invention, imparting the ability to control external devices via brain-derived signals. The present invention can allow disabled patients to not only control an actuator, but it can also permit these patients to perform a range of activities many take for granted, such as walking. The present invention can also assist those patients who, prior to implementation of the present invention, might have never walked or been able to perform tasks with their hands or arms.

Although the present invention does not directly treat a condition giving rise to paralysis or other loss of motor control, the closed loop brain-machine interface offers disabled patients, for the first time, a new option for dealing with their conditions. For example, a paralyzed patient no long need be confined to a wheelchair or to a bed; the present invention might afford this patient the opportunity to walk again, or perhaps for the first time. In another example, the present invention affords a person lacking motor control over his or her arms and/or hands, the ability to move one or more actuators as the patient would move his or her own appendages. Moreover, since the present invention comprises a closed loop, the closed loop brain-machine interface also enables a patient to "feel" and interact with his or her environment in a way heretofore unavailable to the patient.

Summarily, the closed loop brain-machine interface embodies, among other things, a significant advance for patients suffering from impaired motor control over their appendages. The present invention can greatly enhance the quality of life for these patients and can be a benefit for caregivers as well.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Materials and Methods Employed in Laboratory Examples 1–7

The following materials and methods were employed in Laboratory Examples 1–7.

Surgical and Electrophysiological Procedures

Two owl monkeys (*Aotus trivirgatus*) (monkey 1 and monkey 2) received chronic implantations of multiple microelectrode arrays (available from NBLABS of Denison, Tex.), each containing 16–32 TEFLON®-coated, stainless steel microwires (50 μm in diameter) in different cortical areas under general gas anesthesia (1% isofluorane) (Nicolelis et al., (1998) *Nature Neurosci.* 1: 621–630; Laubach et al., (2000) *Nature* 405: 567–571; Nicolelis et al., (1997) *Neuron* 18: 529–537). Stereotaxic coordinates, published microstimulation maps for owl monkeys (Stepniewska et al., (1993) *J. Comp. Neurol.* 330: 567–571; Preuss et al., (1996) *J. Comp. Neurol.* 371: 649–676) and intraoperative neural mapping recordings were used to locate the premotor, primary motor, and posterior parietal cortical areas. During the implantation process, mechanical stimuli were continuously delivered to the arm, face, and legs (including tapping of muscles and passive joint movements) while monitoring neuronal activity in order to identify the rostral and caudal borders of cortical regions in which somatosensory responses could be evoked under anesthesia. Once these borders were established, implants were made in motor cortical areas that were anterior to the rostralmost limit of the somatosensory cortex, and in the parietal cortex immediately posterior to the caudalmost border of the somatosensory cortex.

One to two weeks after this surgical procedure, animals were brought back to the lab and placed in a primate chair within a recording chamber for daily recording sessions. A 96-channel many neuron acquisition processor (MNAP) (available from Plexon, Inc. of Dallas, Tex.) was used to acquire and discriminate activity from single neurons from each implanted microwire (Nicolelis et al., (1997) *Neuron* 18: 529–537). Time-amplitude discriminators and a modified version of a principal component algorithm (Evarts, (1966) *J. Neurophysiol.* 29: 1011–1027) were used to isolate single cortical units in real-time. Analog samples of the action potential waveforms and the time of occurrence of each spike were stored. Continuous recordings were obtained over 12 months for monkey 1 and over 24 months for monkey 2.

Behavioral Tasks

Both owl monkeys were trained and tested on two behavioral tasks. In the first task (task 1), subjects were trained to center a manipulandum for a variable time and then to move it either to left or right targets in response to a visual cue to receive a juice reward. The position of the manipulandum was recorded continuously throughout the session using a precision potentiometer with a sampling rate of 200 Hz. In the second task (task 2), the monkeys were trained to place their right hand on a small platform attached to the chair, located waist high and next to the body. When an opaque barrier was lifted, subjects reached out and grabbed a small piece of fruit from one of four fixed target locations on a tray mounted in front of them. The target locations were positioned in the form of a rectangle, with 6 cm between the left and right locations, and 3 cm between the front and back locations.

To monitor the animals' arm movements in both tasks, the location and orientation of the wrist in three-dimensional space was continuously recorded using a plastic strip containing multiple fiber optic sensors (SHAPE TAPE™, available from Measurand, Inc. of Fredricton, New Brunswick, Canada). This plastic strip was attached to the monkeys' right arm. As each monkey moved its arm, the bending and twisting of the plastic strip modified the transmission of light through the fiber optic sensors, providing an accurate description of wrist position in the X-, Y-, and Z-dimensions. The resulting analog signals were sampled at 200 Hz and converted to 3-D arm trajectories. All sessions were also videotaped.

A Linear Model

Predictions of arm position based on simultaneously recorded ensembles of cortical neurons were obtained by applying both a linear model and an artificial neural network (ANN) to the multi-channel neural data. The first analytical step was to test the validity of the linear model by carrying out offline analysis of data collected in many recording sessions in both monkeys. The employed linear model is an extension of the basic linear regression y=ax+b to the condition where the inputs (x) and outputs (y) are time series. In this case, significant coupling between inputs and outputs is typically not limited to observations that are simultaneous in time, but can exist over some range of time delay or lag between the signals. In this model, X(t) is a matrix of the inputs with each column corresponding to the discharges of individual neurons, and each row representing one time bin. In the 1-D case, Y(t) is a single vector of the outputs, with samples of the position. In the 3-D case, Y(t) is a matrix with three columns, one for each dimension. The linear relationship between the neuronal discharges in X(t), and arm position in Y(t) is expressed as:

$$Y(t) = b + \sum_{u=-m}^{n} a(u)X(t-u) + \varepsilon(t)$$

This equation convolves the series in X(t) (i.e., neuronal firing in time) with the functions a(u), so that the sum of these convolutions, plus a constant, b, approximates the arm trajectory, Y(t). In the equation above, a(u) are the weights required for fitting X(t) to Y(t) as a function of time lag u between inputs and the outputs. These weight functions are called "impulse response functions." There is one impulse response function for each neuron in X(t) and dimension in Y(t) (i.e., with 50 neurons and 3-D movements, there are 150 impulse response functions). The term b represents the y-intercept in the regression. For 1-D movements, b is a single number. For 3-D movements, b is a vector with 3 numbers, one for each dimension. The final term in the equation, $\epsilon(t)$, represents the residual errors, i.e. any variation in Y(t) that cannot be explained by X(t) (Georgopoulos et al., (1982) *J. Neurosci.* 2: 1527–1537; Weinrich & Wise, (1982) *J. Neurosci.* 2: 1329–1345; Wise et al., (1997) *Annu. Rev. Neurosci.* 20: 25–42).

The limits of the time lag u (m and n in the above equation) are set so that time lags for which statistically significant coupling exists between the signals in X(t) and V(t) are included in the model. The desired values of m and n can be estimated initially with large numbers (e.g., 5–10 seconds) and then can be further refined by evaluating the impulse response functions statistically over many data sets. In the present disclosure, these impulse response functions were significantly different from zero for time lags of up to one second in some cortical neurons.

Action potentials from the neurons were treated as point processes and the position of the monkey's wrist in one or three dimensions was considered as realizations of continuous processes. The sampling rate was 200 Hz, corresponding to time bins of 5 milliseconds. Direct time-domain calculation of impulse response functions at such high temporal resolution is computationally very difficult. Therefore, the impulse response was calculated off-line using a frequency-domain approach, which is described in detail elsewhere (Brillinger, (1981) *Time Series. Data Analysis and Theory*, Holden-Day, San Francisco, Calif.; Halliday et al., (1995) *Prog. Biophys. Mol. Biol.* 64: 237–278). Briefly, this off-line procedure consisted of the following steps. First, the auto-spectra (i.e., power spectra) for all input and output signals, as well as the cross-spectra between all pairs of signals were calculated by standard procedures using a Fast Fourier transformation (FFT) of synchronous segments of all signals and averaging over all segments in the data set used for fitting the mode (Halliday et al., (1995) *Prog. Biophys. Mol. Biol.* 64: 237–278; Powell, (1977) *Math. Program.* 12: 241–254; Ghazanfar et al., (2000) *J. Neurosci.* 20: 3761–3775). This first step yields a spectral density matrix, $f(\lambda)$, which is the frequency-domain analog of the covariance matrix between all the input and output variables. The spectral density matrix can be partitioned into $f_{XX}(\lambda)$ and $f_{YX}(\lambda)$, where $\lambda$ denotes frequency $f_{XX}(\lambda)$ describes the frequency-domain relations between all the inputs in X(t) and $f_{YX}(\lambda)$ describes the relations between the outputs Y(t) and the inputs X(t). The remaining parts of $f(\lambda)$, $f_{YY}(\lambda)$ and $f_{XY}(\lambda)$, are not used. Next, the transfer functions between the frequency-domain analog of the inputs signals in X(t) and the output signals in Y(t) can be calculated by the equation:

$$A(\lambda) = f_{YX}(\lambda) f_{XX}(\lambda)^{-1}$$

where "to the power of minus unity" indicates a matrix inverse. The transfer functions in the matrix $A(\lambda)$ describe the gain and phase relations between each pair of input-output signals as a function of frequency. Next, the impulse response functions a(u) are equivalent to the inverse Fourier transforms of the transfer functions, and hence they can be easily calculated using the FFT algorithm (Georgopoulos et al., (1982) *J. Neurosci.* 2: 1527–1537; Weinrich & Wise, (1982) *J. Neurosci.* 2: 1329–1345; Wise et al., (1997) *Annu. Rev. Neurosci.* 20: 25–42). Finally, the y-intercept constants b are estimated by the relation $$b = aver\{Y(t)\} - A(0) aver\{X(t)\}$$

where the averages indicate the sample means for each of the signals in X(t) and Y(t).

To evaluate coupling between the activity of individual neurons and arm position (either in 1-D, or for each of the three dimensions separately in 3-D), coherence spectra were calculated. Spectra and cross-spectra for pairs of signals were calculated as described above, that is, by Fourier transformation of segments of data, and averaging over all available segments. Using 2-second segments, a spectral resolution of 0.5 Hz was obtained. The spectrum for a single neuron is $f_{XX}(\lambda)$, the spectrum for the position is $f_{YY}(\lambda)$, and the cross-spectrum between the two is $f_{XY}(\lambda)$. The coherence spectrum is defined as $$|R_{xy}(\lambda)|^2 = \frac{|f_{xy}(\lambda)|^2}{f_{xx}(\lambda) f_{yy}(\lambda)}$$

i.e., the coherence spectrum is the squared absolute cross-spectrum between the two signals normalized by their autospectra. The coherence spectrum describes the degree of linear coupling between the two signals as a function of frequency, on a scale from zero to one. Statistical evaluation of significance of the coherence spectrum was done using standard methods, which are described elsewhere (Georgopoulos et al., (1982) *J. Neurosci.* 2: 1527–1537; Wise et al., (1997) *Annu. Rev. Neurosci.* 20: 25–42).

A Linear Model in Real-time

When the off-line analysis was completed, a slightly modified linear model was employed for real-time prediction of arm movements. First, data corresponding to a time lag from Y(t) (arm position) to X(t) (neuronal activity), representing potential feedback (e.g. proprioceptive) information generated by the arm movements, was not available for real-time predictions of Y(t). In other words, to predict Y(t) instantaneously, one should use past neuronal activity to predict future arm movements. Second, to reduce the real-time computational load, and due to limitations in the computer resources available (dual 800 MHz Pentium III, PC compatible microcomputer) the temporal resolution of the off-line model was reduced. Instead of treating the neuronal activity as a point process at 200 Hz, the number of discharges for each neuron was counted in 100 millisecond bins, corresponding to 10 Hz. To account for neuronal activity for lags of up to one second before the arm position signals, ten such bins per neuron were used in the model. The sampling of the position signals were correspondingly reduced to 10 Hz, which was permissible because the position signals were very smooth and contained only negligible variance in the spectra above 5 Hz. The complete model for real-time hand positions is $$Y(t) = b + \sum_{u=0}^{9} a(u) X(t-u) + \varepsilon(t)$$

where the time variables t and u are in units of samples, i.e. 10 per second. There were ten "copies" of X(t) used in the model, one for each integer value of u, from 0 to 9. In other words, there were ten times as many inputs in this equation as there are neurons in X(t), each input corresponding to one appropriately time-shifted copy of each neuron in X(t). If we create a new matrix with all the copies of the neurons, X'(t), the equation becomes $$Y(t) = b + a' X'(t) + \epsilon(t)$$

The weights a' and the Y-intercept b can in this case be estimated directly in the time-domain using standard linear regression techniques.

An Artificial Neural Network (ANN) Model

The same data structure described for the real-time version of the linear model was employed, i.e. the inputs were up to ten 100 ms bins of counts of neuronal discharges for each of the recorded neurons. All tested ANNs were feedforward networks in which the neuronal signals were processed by a nonlinear hidden layer of units, which used the so-called tan-sigmoid output function (Mitz et al., (1991) *J. Neurosci.* 11: 1855–1872), that fed into a linear output layer that predicted the position signals. There was one output for ANNs used for estimating position in 1-D, and three outputs for 3-D movements. Several different algorithms for training the networks were evaluated off-line: classical backpropagation with variable learning rates, resilient backpropagation (Humphrey et al., (1970) *Science* 170: 758–762), backpropagation using the Fletcher-Reeves and Polak-Ribiere variants of the conjugate gradient algorithm (Georgopoulos et al., (1986) *Science* 233: 1416–1419), the Fletcher-Reeves algorithm with Powell-Beale restarts (Mitz et al., (1991) *J. Neurosci.* 11: 1855–1872; Schwartz, (1994) *Science* 265: 540–542), and the scaled conjugate gradient algorithm (Fetz & Cheney, (1980) *J. Neurophysiol.* 44: 751–772). A quasi-Newton method (Nicolelis et al., (1998) *Nature Neurosci.* 1: 621–630) and the Levenberg-Marquart method (Laubach et al., (2000) *Nature* 405: 567–571) were tested as well, but were found to require too much RAM memory to allow PC-compatible computers to be used efficiently. Empirically, it was found that the fastest fitting of the models and the best predictions of hand position were obtained using one hidden layer with 15–20 units, and the Powell-Beale method (Mitz et al., (1991) *J. Neurosci.* 11: 1855–1872; Schwartz, (1994) *Science* 265: 540–542). In addition, an early stopping rule was used to avoid overfitting of the data used for training the network and to improve predictions with new data (Mitz et al., (1991) *J. Neurosci.* 11: 1855–1872).

The position predictions obtained in real-time with ANNs were comparable to those obtained with using the linear algorithm. During off-line analysis, the ANN model was often a few percent better than the corresponding linear model for the same data set. During most real-time sessions, any such advantage appeared to be offset by the slightly longer time it took to fit the ANN models compared to the linear model.

Real-time Prediction of Hand Position

Real-time analysis also included an adaptive routine, which allowed us to carry out repeatedly an unsupervised fitting of both linear and ANN models throughout the recording session. Thus, the first minute of data in each recording session was used to compute the first version of both linear and ANN models using two separate computers. The resulting fitted models were then sent back to the data acquisition computer where the arm position was instantaneously and continuously predicted using the neuronal ensemble firing data acquired in real-time. During the remainder of the experimental session, both models continued to be repeatedly calculated as fast as possible, using the most recently recorded 10 minutes of data. Depending on the number of active neurons, the models usually took 2–15 minutes to be fitted using dual 800 MHz PC-compatible computers. All calculations were performed by software designed in MATLAB (The Mathworks, Natick, Mass.).

Real-time Control of Robot Arms

As the results from the two mathematical models became available, they were broadcasted via a standard Internet protocol (transfer control protocol/internet protocol, TCP/IP) server to one or more computer clients. One client used these data to control the movements of a robot arm located in our laboratory at Duke University (PHANTOM™ Model A1.0 available from SensAble Technologies, Inc. of Woburn, Mass.) (Nicolelis et al., (1997) *Neuron* 18: 529–537) where all recording sessions were carried out. Simultaneously, another client located at the Massachusetts Institute of Technology (PHANTOM™ Desktop, available from SensAble Technologies, Inc. of Woburn, Mass.) controlled the movements of a remote robot arm. As the robots moved, a signal describing their position in space was recorded on each client machine, so that the accuracy with which both local and remote robot arm movements matched the arm trajectory signals generated by the models could be measured.

Both robots were high-precision serial link manipulators with three actuated degrees of freedom. Each joint angle was sensed by an optical encoder (4000 counts per revolution) co-located with the shaft of the DC motor actuating the joint. This arrangement provided a nominal position resolution at the robot tip of 0.02 mm for the Desktop PHANTOM™ and 0.03 mm for the PHANTOM™ 1.0A. The motors were controlled through a 12-bit digital-analog converter, which provided a nominal force resolution at the robot tip of 1.6 mN for the Desktop PHANTOM™ and 2.1 mN for the PHANTOM™ 1.0A.

The input command to the robots was the Cartesian coordinates of the end-effector. The transformation between changes in end-effector coordinates and changes in robot joint angles (i.e., the Jacobean) was performed by the robot manufacturer's low-level control code. Standard PD (Position-Derivative) control of the end-effector coordinates was implemented in the C++ programming language. Control gains were tuned by hand for each of the robots to ensure that the end-effector followed the commanded trajectory with minimal errors in a stable manner. A new coordinate was commanded every 100 ms, based on the monkey's neural output. The command was interpolated between updates in order to match the normal (1 kHz) servo rate of the robots.

LABORATORY EXAMPLE 1

Implantation of Microwire Arrays

Microwire arrays were implanted in multiple cortical areas of two owl monkeys (*Aotus trivirgatus*) (Nicolelis et al., (1998) *Nature Neurosci.* 1: 621–630; Laubach et al., (2000) *Nature* 405: 567–571; Nicolelis et al., (1997) *Neuron* 18: 529–537). In the first monkey, 96 microwires were implanted in the left dorsal premotor cortex (PMd, 16 wires), left primary motor cortex (MI 16) (Stepniewska et al., (1993) *J. Comp. Neurol.* 330: 238–271; Preuss et al., (1996) *J. Comp. Neurol.* 371: 649–676), left posterior parietal cortex (PP, 16) right PMd and MI (32) andd right PP cortex (16). In the second monkey, 32 microwires were implanted in the left PMd (16) and in the left MI (16).

LABORATORY EXAMPLE 2

Recording of Cortical Neural Ensembles

Recordings of cortical neural ensembles began 1–2 weeks after the implantation surgery and continued for 12 months in monkey 1, and 24 months in monkey 2. During this period, the monkeys were trained in two distinct motor tasks. In task 1, animals made one-dimensional (1-D) hand movements to displace a manipulandum in one of two directions (left vs. right) following a visual cue. In task 2, the monkeys made three-dimensional (3-D) hand movements to reach for small pieces of food randomly placed at four different positions on a tray. Cortical recordings were obtained while the two subjects were trained and tested on both tasks (FIG. 1A).

Figure 1B:
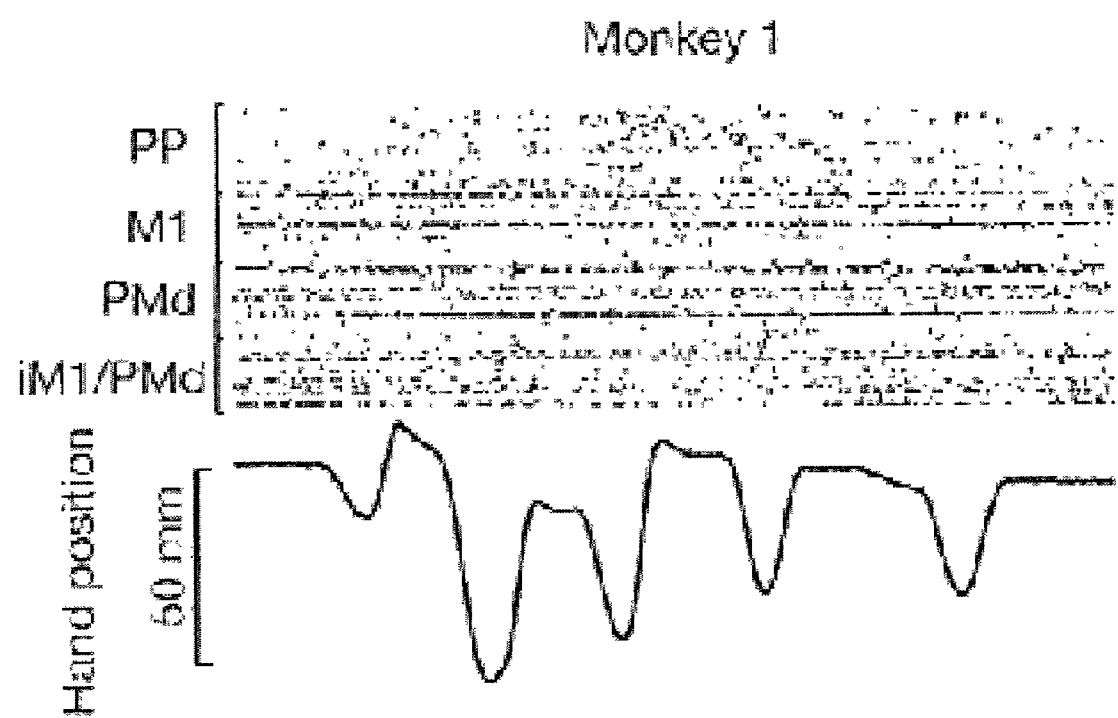
FIG. 1B are traces depicting simultaneously recorded neuronal activity in five cortical areas of Monkey 1 during the execution of 1-D movements.
Figure 1C:
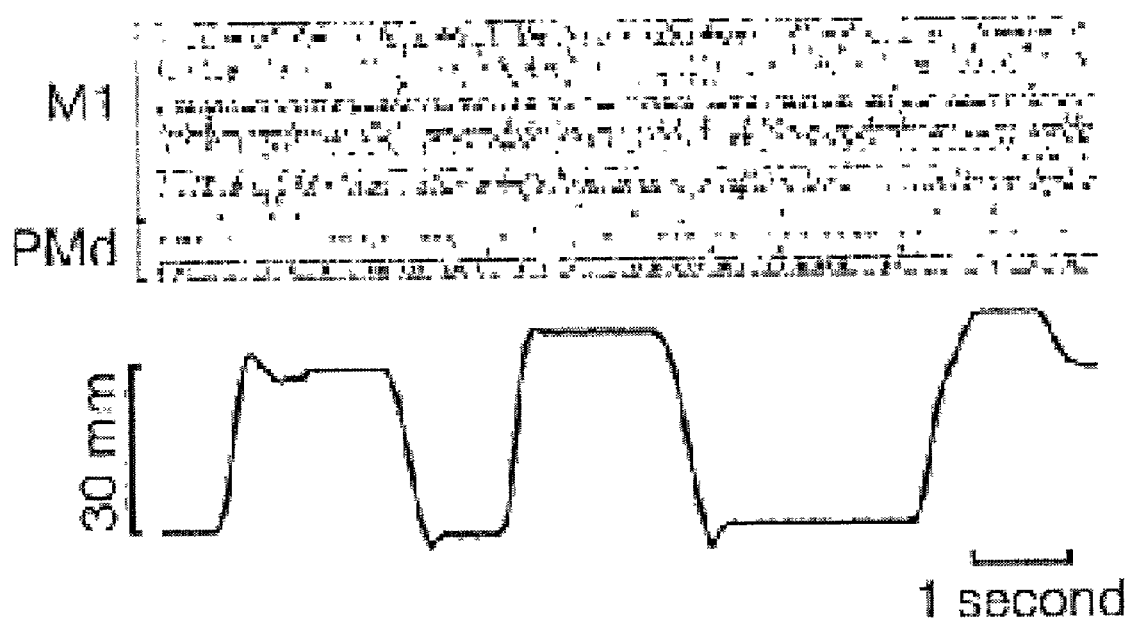
FIG. 1C are traces depicting simultaneously recorded neuronal activity in two cortical areas of Monkey 2 during the execution of 1-D movements.
Figure 2A:
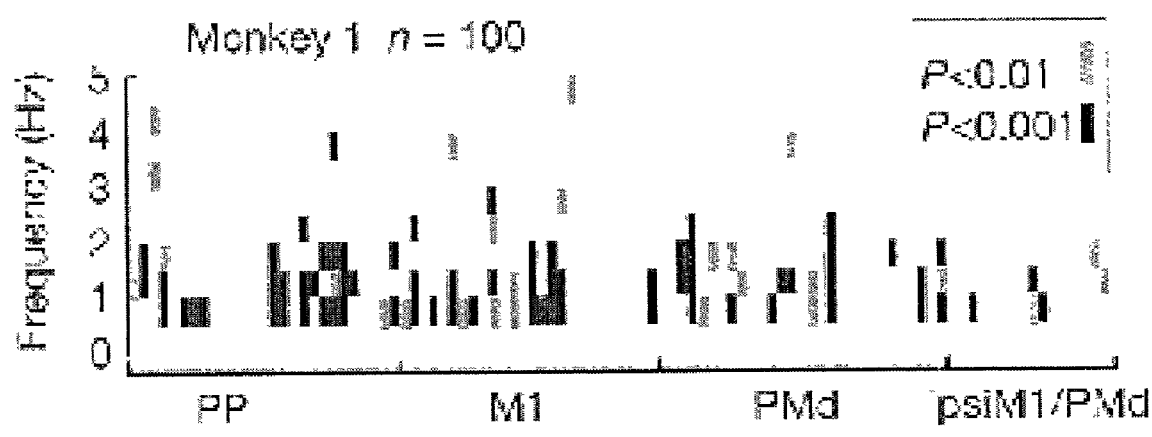
FIG. 2A is coherence analysis depicting significant coupling of most cortical neurons with different frequency components of 1-D hand movements in Monkey 1.
Figure 2B:
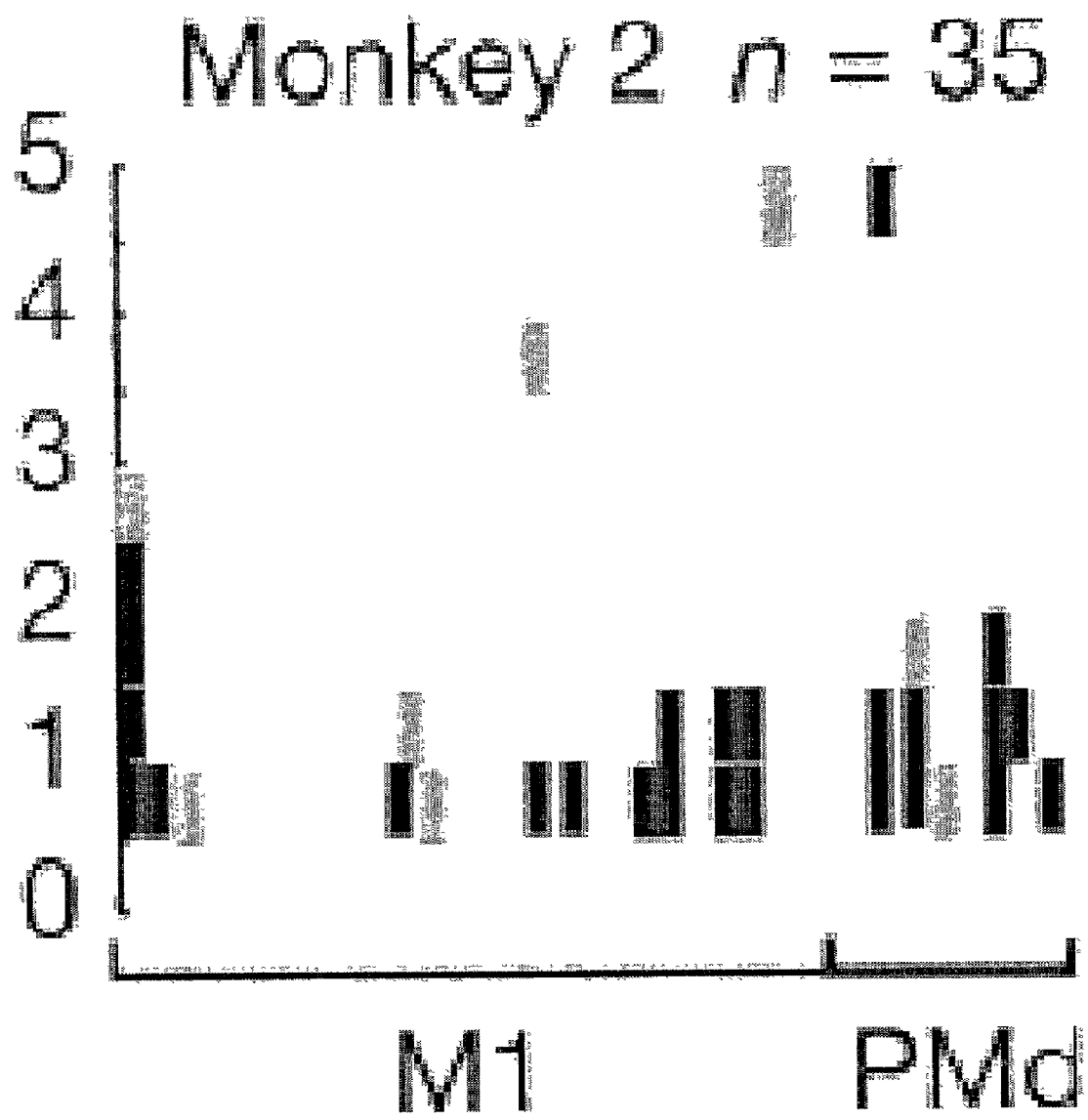
FIG. 2B is coherence analysis depicting significant coupling of most cortical neurons with different frequency components of 1-D hand movements in Monkey 2.

FIGS. 1B–1C illustrate samples of the raw neuronal data obtained while the animals performed task 1. In both monkeys, coherence analysis (Brillinger, (1981) *Time Series. Data Analysis and Theory*, Holden-Day, San Francisco, Calif.; Bendat & Piersol, (1986) *Random Data. Analysis and Measurement Procedures*, Wiley, New York, N.Y.; Halliday et al., (1995) *Prog. Biophys. Mol. Biol.* 64: 237–278) revealed that the activity of most single neurons from each of the simultaneously recorded cortical areas was significantly correlated with both 1-D (FIGS. 2A–2B) and 3-D hand trajectories, although the degree and frequency range of these correlations varied considerably within and between cortical areas.

LABORATORY EXAMPLE 3

Application of Algorithms

Figure 2C:
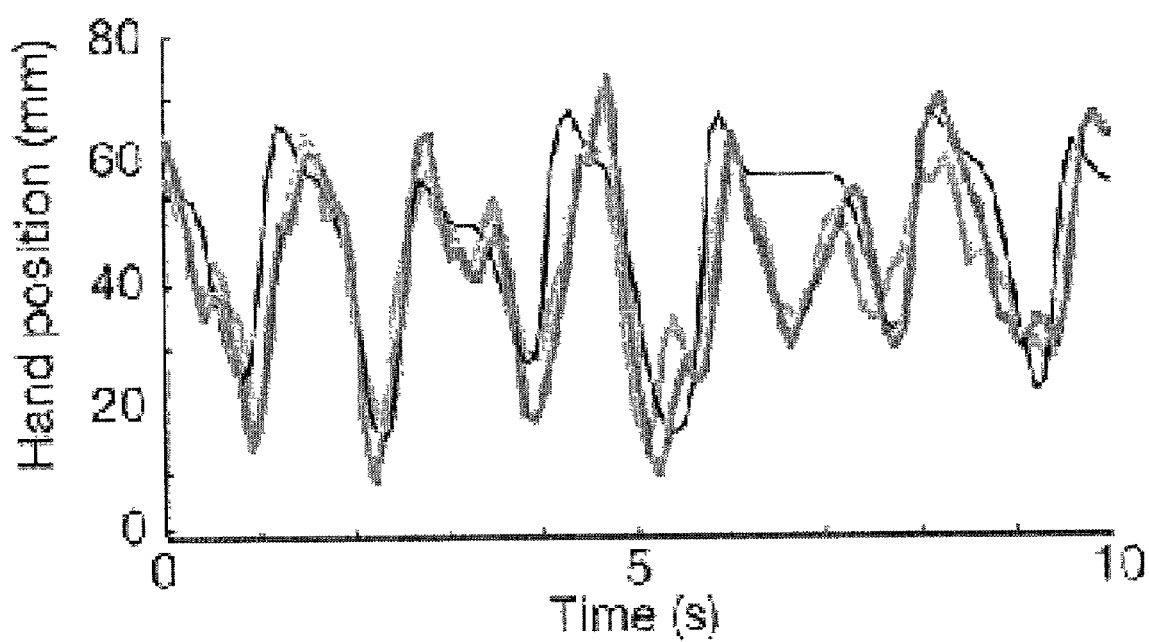
FIG. 2C is a plot depicting observed (thick black line) and real time predicted 1-D hand movements using both linear (thin back line) and ANN (gray line) models in Monkey 1.
Figure 2D:
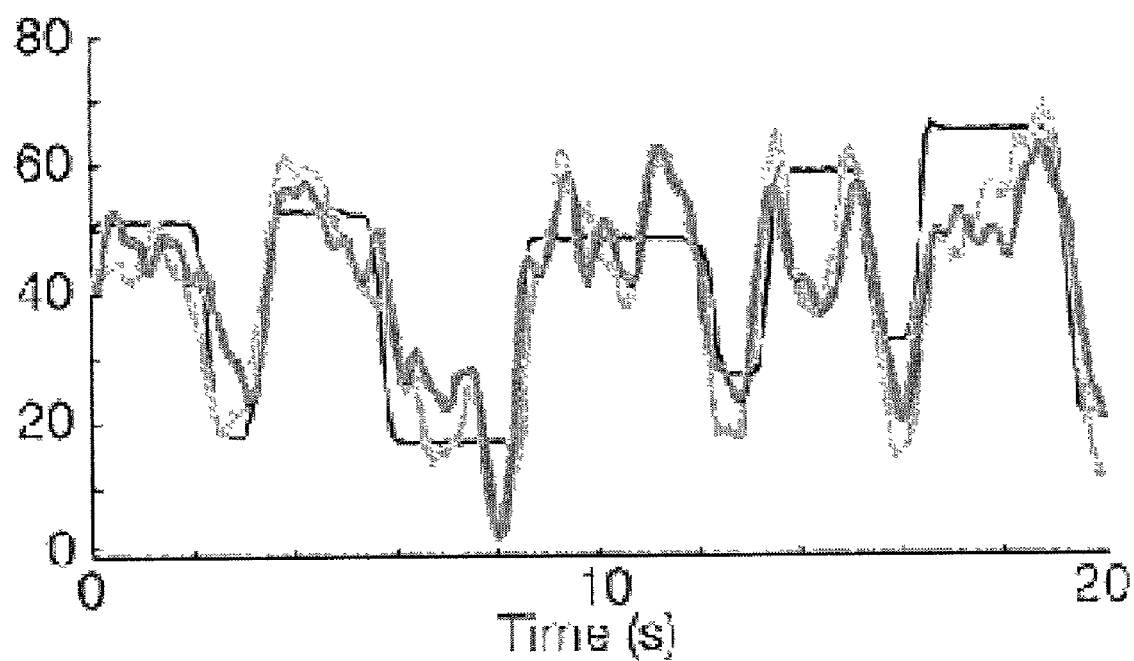
FIG. 2D is a plot depicting observed (thick black line) and real time predicted 1-D hand movements using both linear (thin back line) and ANN (gray line) models in Monkey 2.
Figure 2E:
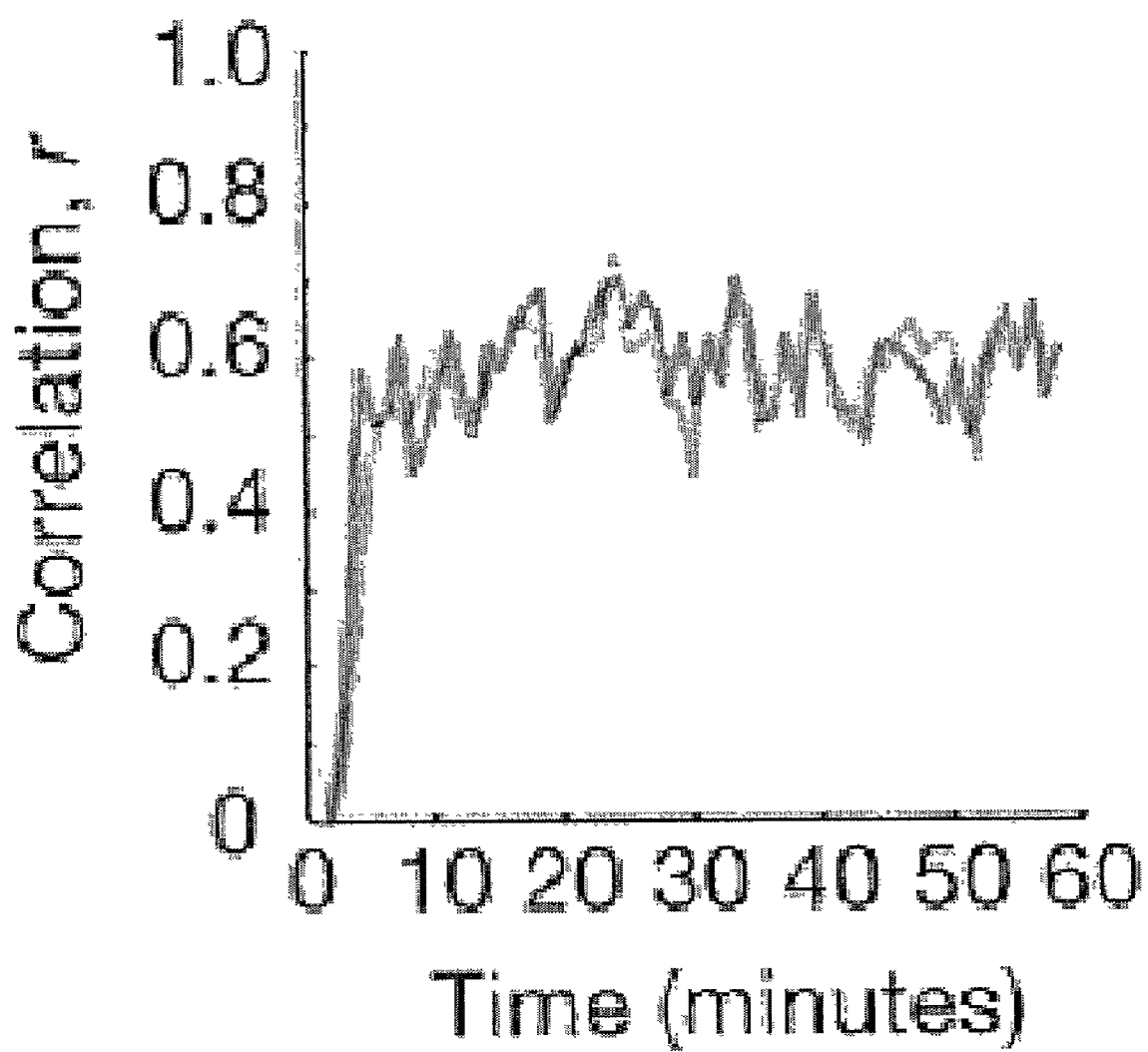
FIG. 2E is a plot depicting correlation coefficient variation for predicted hand movements, using linear (gray line) and ANN (black line) models in one recording session in Monkey 1.
Figure 2F:
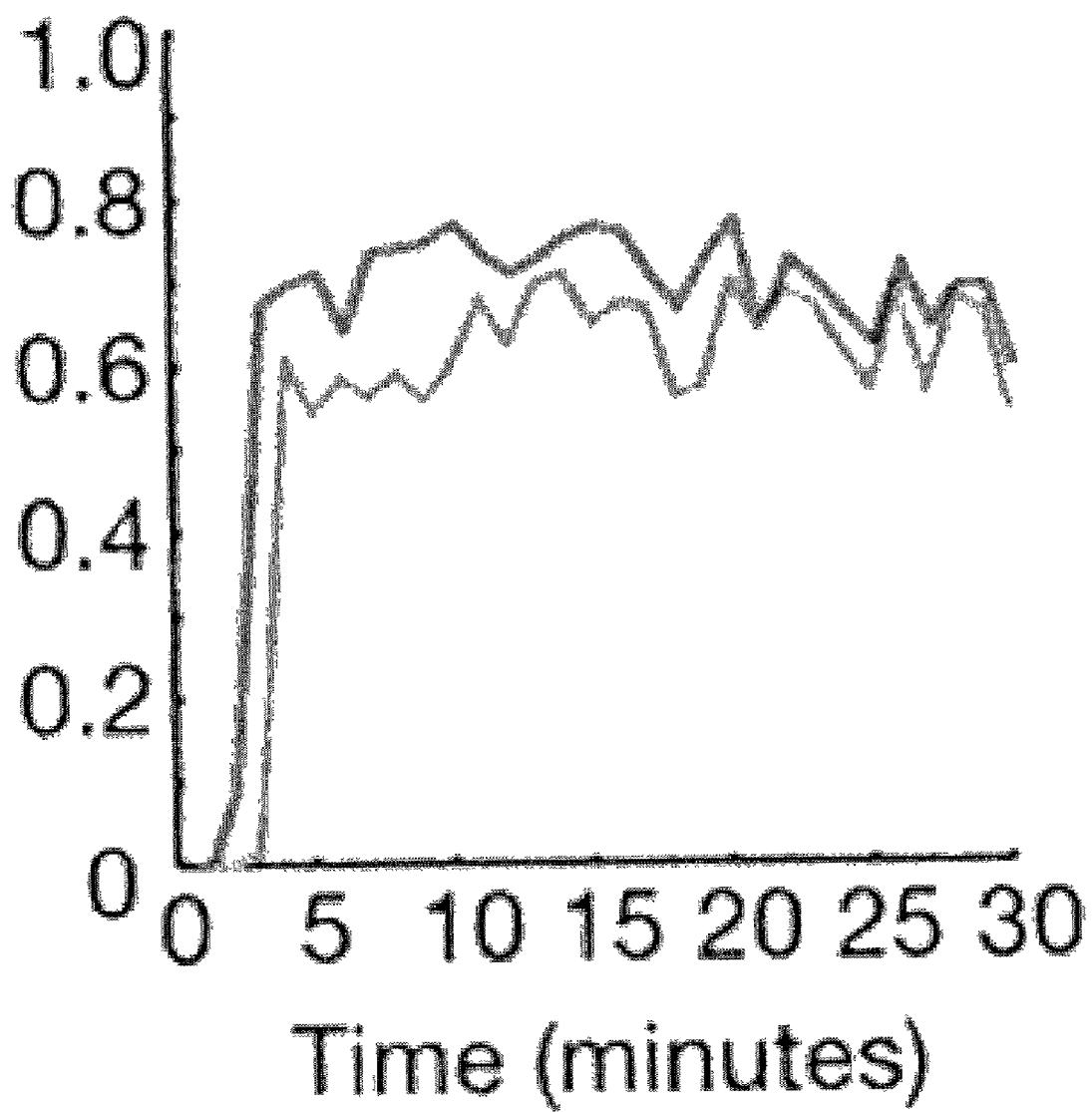
FIG. 2F is a plot depicting correlation coefficient variation for predicted hand movements, using linear (gray line) and ANN (black line) models in one recording session in Monkey 2.

It was then investigated whether both linear (Brillinger, (1981) *Time Series. Data Analysis and Theory*, Holden-Day, San Francisco, Calif.; Bendat & Piersol, (1986) *Random Data. Analysis and Measurement Procedures*, Wiley, New York, N.Y.; Halliday et al., (1995) *Prog. Biophys. Mol. Biol.* 64: 237–278) and artificial neural network (ANN) (Powell, (1977) *Math. Program.* 12: 241–254; Ghazanfar et al., (2000) *J. Neurosci.* 20: 3761–3775) algorithms could be used to predict hand position in real-time. For 1-D movements, it was observed that both algorithms yielded highly significant real-time predictions in both monkeys (FIGS. 2C–2D). These results were obtained in spite of the fact that the trajectories were quite complex, involving different starting positions, as well as movements at different velocities. For example, in the session represented in FIG. 2C, the activity of 27 PMd, 26 MI, 28 PP, and 19 ipsilateral MI/PMd neurons in monkey 1 allowed an average correlation coefficient of 0.61 between the observed and predicted hand position (60 minute session, range 0.50–0.71, linear model; 0.45–0.73, ANN; $p<0.001$ (Brillinger, (1981) *Time Series. Data Analysis and Theory*, Holden-Day, San Francisco, Calif.; Bendat & Piersol, (1986) *Random Data. Analysis and Measurement Procedures*, Wiley, New York, N.Y.; Halliday et al., (1995) *Prog. Biophys. Mol. Biol.* 64: 237–278). FIG. 2D illustrates similar real-time results obtained by using a smaller sample of neurons (8 PMd and 27 Ml) in monkey 2 (average $r=0.72$, range 0.47–0.79, linear model; average $r=0.66$, range 0.42–0.71, ANN, $p<0.001$). No major differences in fitting accuracy were observed between linear and ANN algorithms in either animal (FIGS. 2C–2D, linear prediction, thin black line, ANN, gray line line). As shown in FIG. 2E (monkey 1) and FIG. 2F (monkey 2), the performance of both algorithms improved in the first few minutes of recordings and then reached an asymptotic level that was maintained throughout the experiment. In both monkeys, highly significant predictions of hand movement trajectories were obtained for several months.

To reduce the influence of dynamic changes in the coupling between neuronal activity and movements and other non-stationary influences in our real-time predictions, both linear and ANN models were continuously updated throughout the recording sessions. This approach significantly improved the prediction of hand trajectories. For example, when predicting the last 10 minutes of 50–100 minute sessions, the adaptive algorithm performed 55% (20 sessions, median) better than a fixed model based on the initial 10 minutes, or 20% better than a model based on the 30–40 minute segment.

LABORATORY EXAMPLE 4

Control of a Robot Arm

Figure 2G:
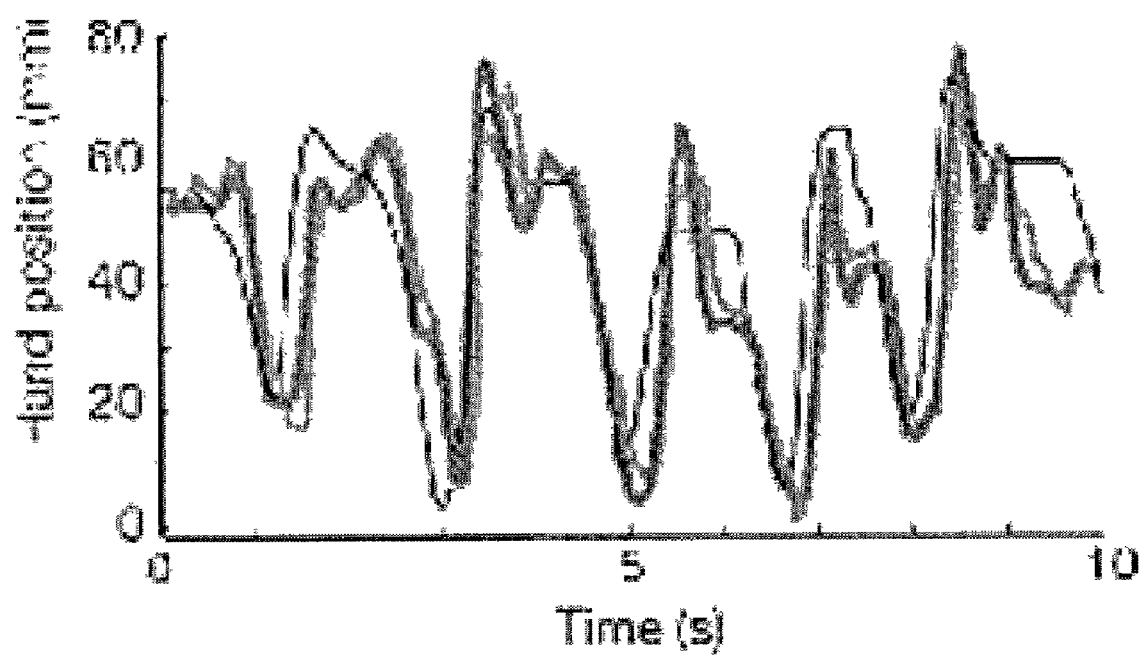
FIG. 2G is a plot depicting real-time 1-D movements of a local (thin black line) and remote (gray line) robot arm obtained in Monkey 1 by using a linear model. (The thick black line represents observed position.)

Because accurate hand trajectory predictions were achieved early on in each recording session and remained stable for long periods of time, it was possible to use brain-derived signals to control the movements of robotic devices (Phantom™, available from SensAble Technologies of Woburn, Mass.) in real-time (FIG. 2G). In addition, it was possible to broadcast these motor control signals to multiple computer clients by using a regular Internet communication protocol (TCP/IP, FIG. 1A) and control two distinct robots simultaneously: one at Duke University (FIG. 2G, thin black line) and one at MIT (FIG. 2G, gray line).

LABORATORY EXAMPLE 5

Prediction of Complex 3-D Movements

Figure 3A:
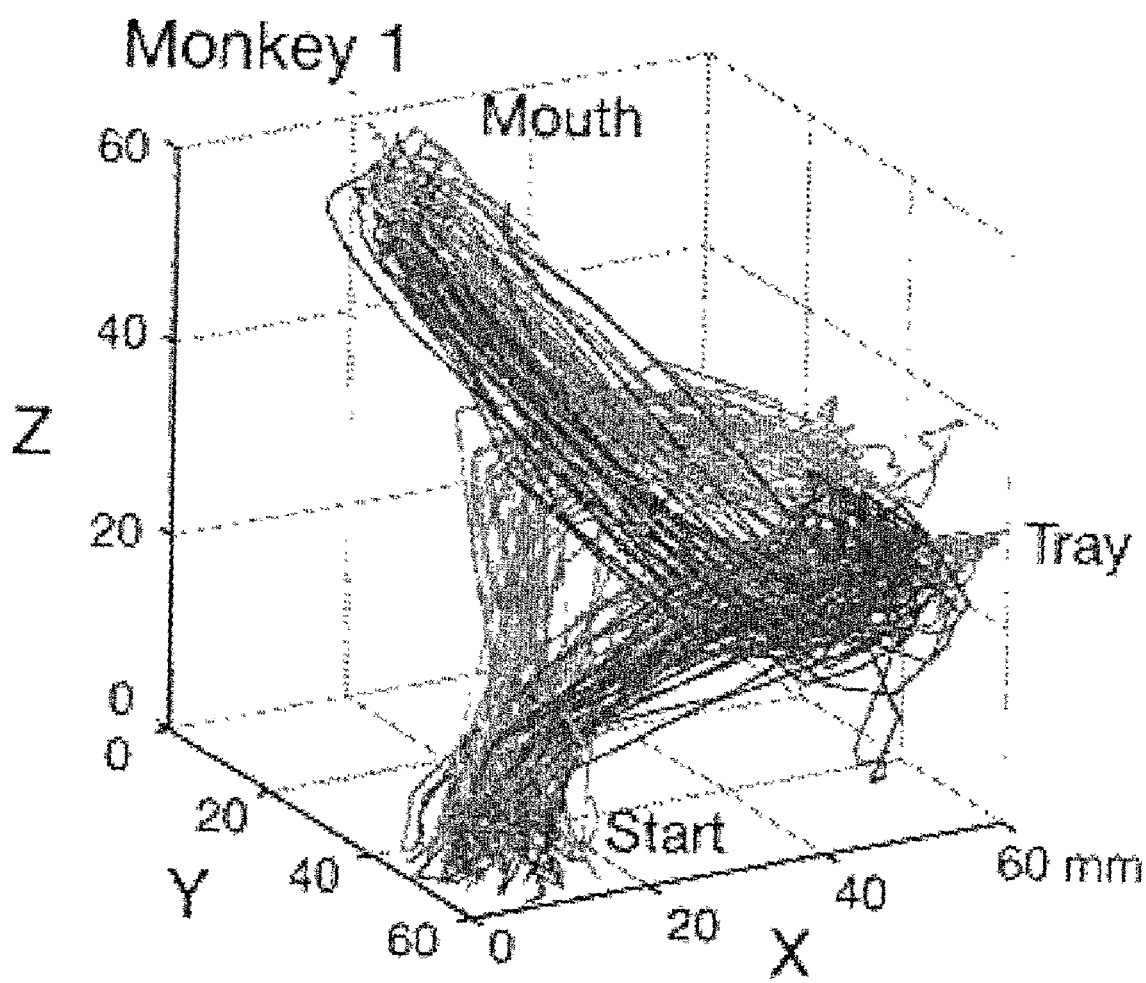
FIG. 3A is a three-dimensional plot depicting 3-D hand movement trajectories produced by Monkey 1 during single experimental sessions.
Figure 3B:
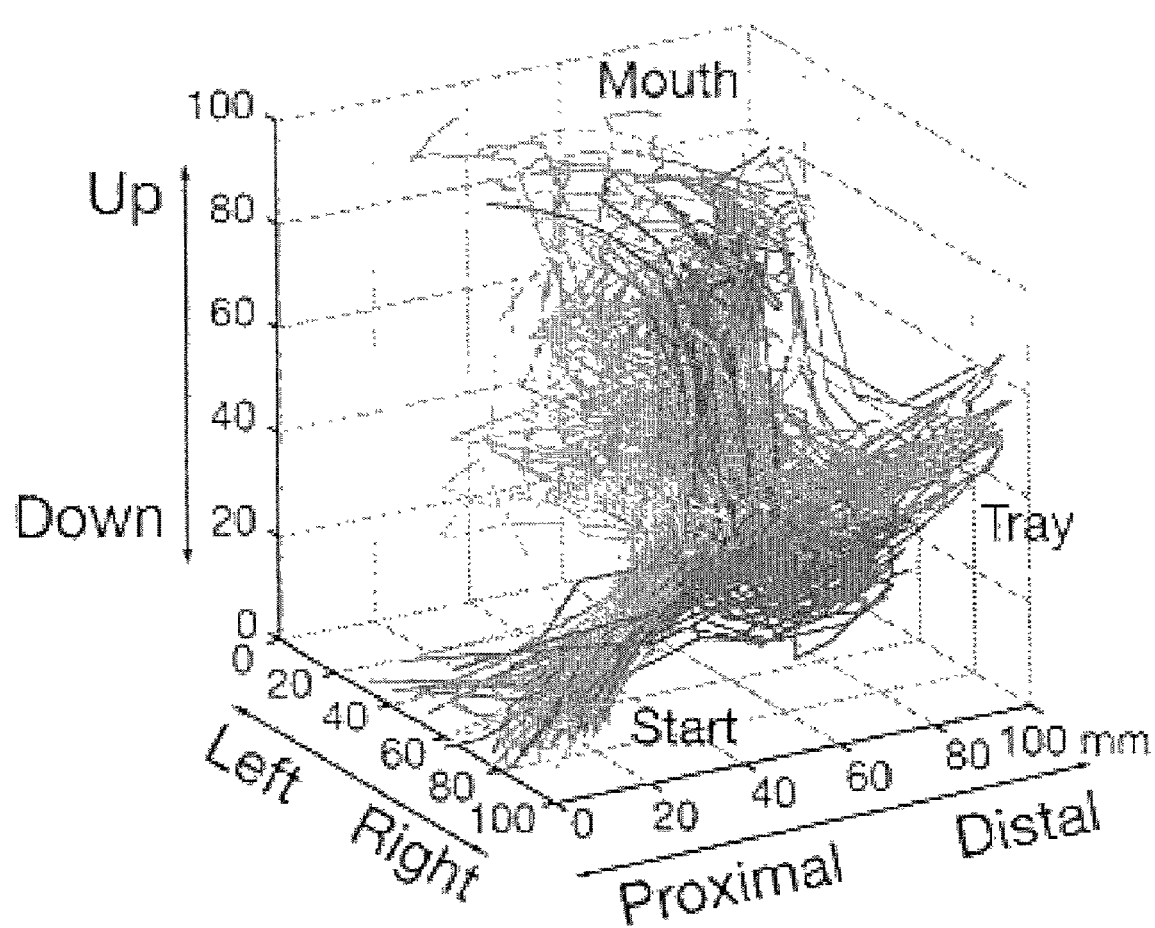
FIG. 3B is a three-dimensional plot depicting 3-D hand movement trajectories produced by Monkey 2 during single experimental sessions.
Figure 3C:
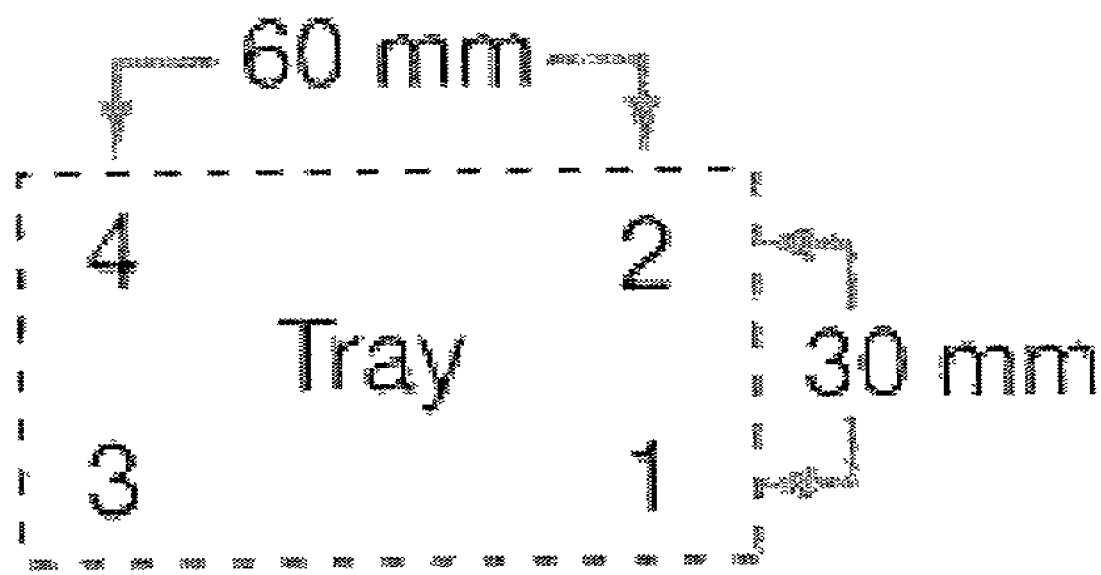
FIG. 3C is a schematic diagram of the four possible target locations in a food reaching task.
Figure 3D:
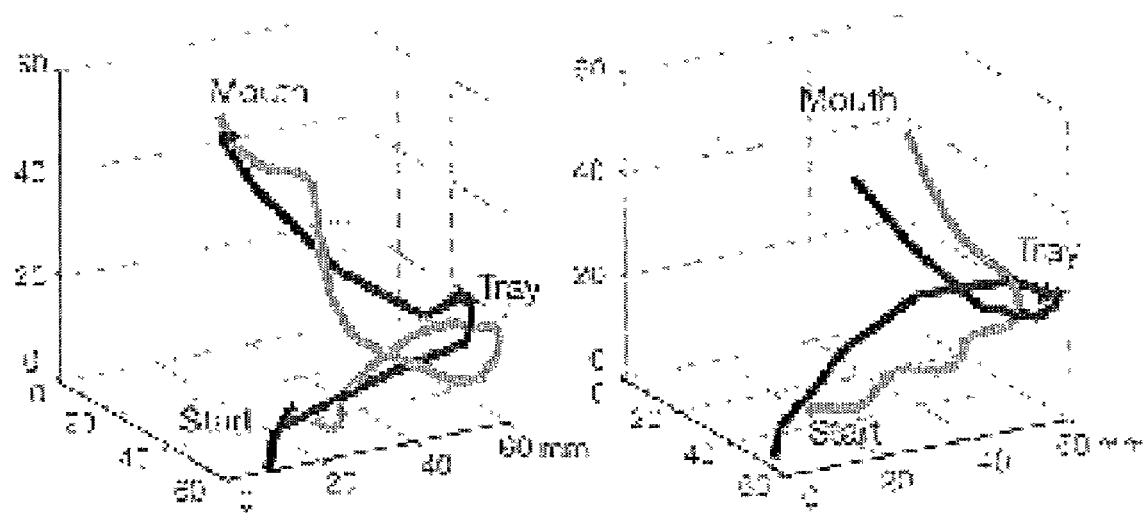
FIG. 3D is a three-dimensional plot depicting samples of observed (black line) and real time predicted (gray line) 3-D hand movement for Monkey 1.
Figure 3E:
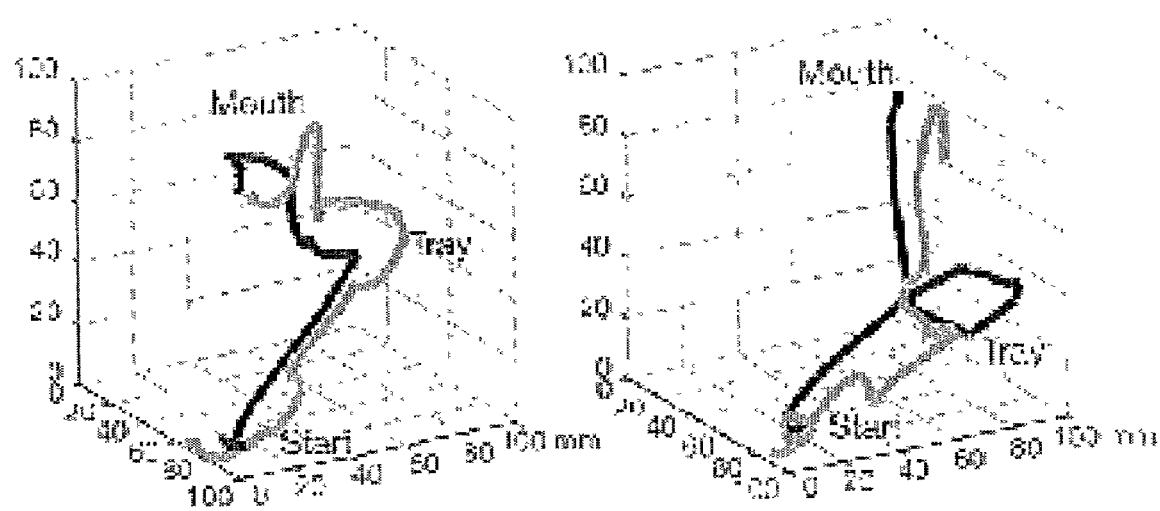
FIG. 3E is a three-dimensional plot depicting samples of observed (black line) and real time predicted (gray line) 3-D hand movement for Monkey 2.
Figure 3F:
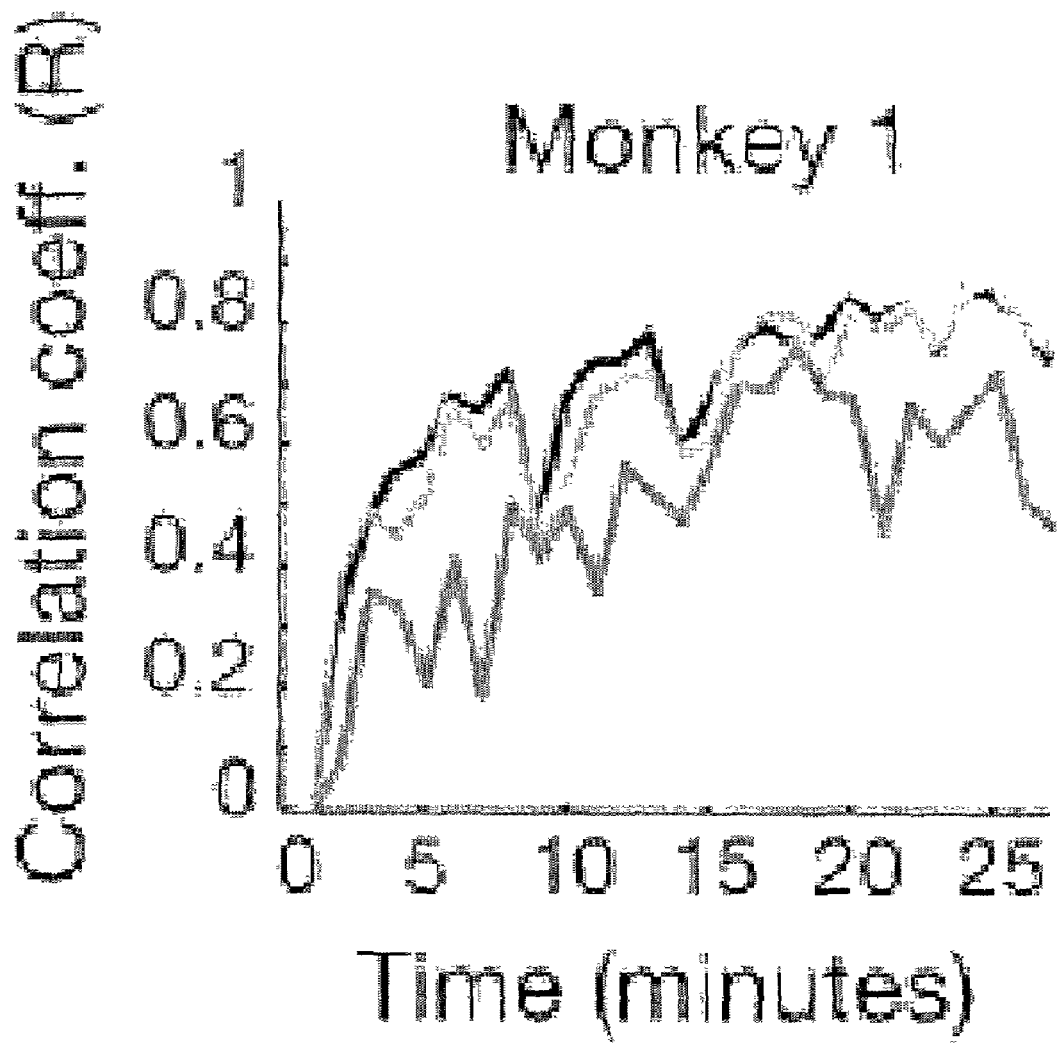
FIG. 3F is a plot depicting correlation coefficient variation for x (thick black line), y (gray line) and z (thin black line) dimensions of predicted 3-D hand movements using a linear model for monkey 1.
Figure 3G:
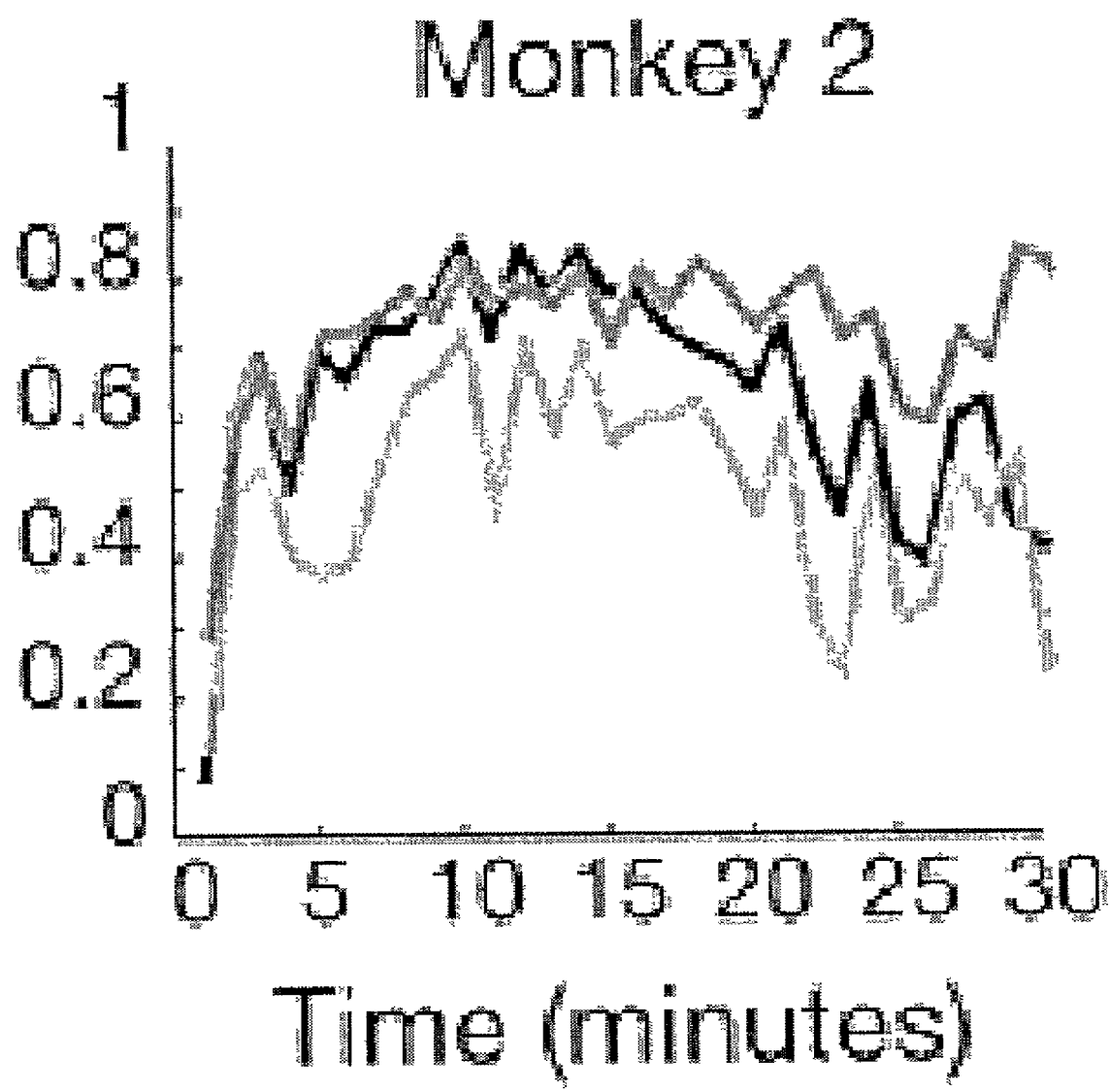
FIG. 3G is a plot depicting correlation coefficient variation for x (thick black line), y (gray line) and z (thin black line) dimensions of predicted 3-D hand movements using a linear model for monkey 2.

The question of whether the same cortical ensemble activity and models could be used to predict the complex sequences of 3-D hand movements used by primates in a food-reaching task (task 2) was then addressed. These movements involved four phases: reaching for the food, grasping the food, bringing the food to the mouth, and returning to the start position (FIGS. 3A–3B). FIG. 3C depicts a schematic of the diagram of the four possible target locations in a food reaching task. Since these animals were not overtrained, their movement trajectories were highly variable. For example, in the session represented in FIG. 3A (monkey 1) the dispersion of hand trajectories was 7.0 by 7.5 by 6.0 cm (or 315 cm$^3$); in FIG. 3B (monkey 2) the dispersion was even bigger, 11.5 by 10.5 by 10.0 cm (or 1207.5 cm$^3$). Nonetheless, in both animals, the same linear and ANN models described above provided accurate predictions of 3-D hand trajectories in 4 different directions during 25–60 minute experimental sessions (60–208 trials). FIGS. 3D–3E illustrate several examples of observed (black lines) and predicted (gray lines) sequences of 3-D movements produced by monkey 1 (FIG. 3D) and 2 (FIG. 3E). After initial improvements, the predictions of 3-D hand trajectories reached asymptotic levels that were maintained throughout the experiments (FIGS. 3F–3G). The 3-D predictions were comparable to those obtained for 1-D movements (monkey 1: $r=0.74$, 0.72, and 0.56 for the X-, Y-, and Z-dimensions respectively; monkey 2: $r=0.70$, 0.54, and 0.77; 20 minute averages).

LABORATORY EXAMPLE 6

Extension of the Model Parameters to Other Directions

Further demonstration of the robustness of our real-time approach was obtained by investigating how well model parameters obtained for one set of hand movements could be used to predict hand trajectories to other directions. For example, by training our linear model only with hand movements directed to targets on the right (targets 1 and 2) we were able to accurately predict hand trajectories to targets on the left (targets 3 and 4). The same was true for the reverse case, i.e. using parameters derived from left movements to predict movements to the right (monkey 1, $r=0.80$, 0.70, 0.67 for the x-, y- and z-dimensions; monkey 2, $r=0.68$, 0.53, 0.81; averages for both conditions). Predictions of distal (targets 2 and 4) movements by training the model only with proximal (targets 3 and 1) hand trajectories and vice versa were comparably accurate (monkey 1, $r=0.81$, 0.71, 0.74 for the x-, y- and z-dimensions; monkey 2, $r=0.69$, 0.63, 0.79; averages).

LABORATORY EXAMPLE 7

Neuron Dropping Experiments

Figure 4A:
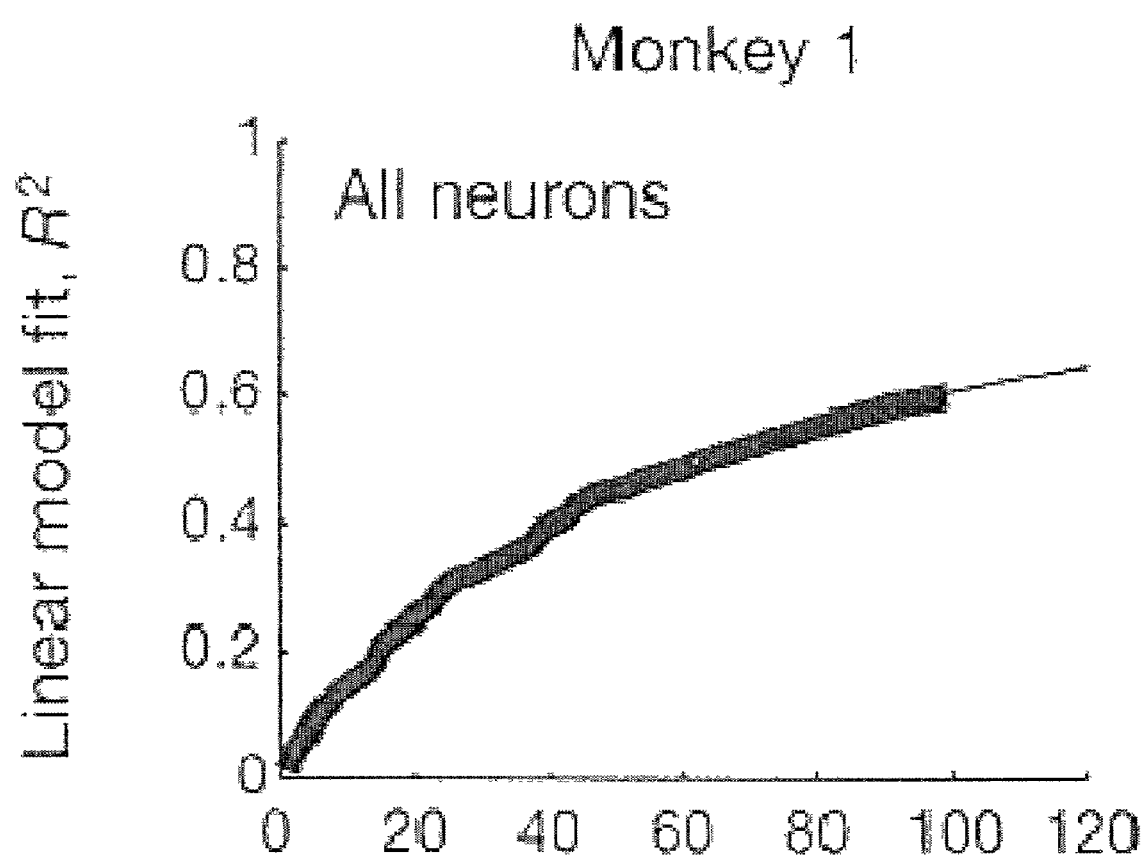
FIG. 4A is a plot depicting a neuron-dropping curve (black line) obtained in a singe session for all cortical neurons in Monkey 1, which is precisely fitted by a hyperbolic function (gray line).
Figure 4B:
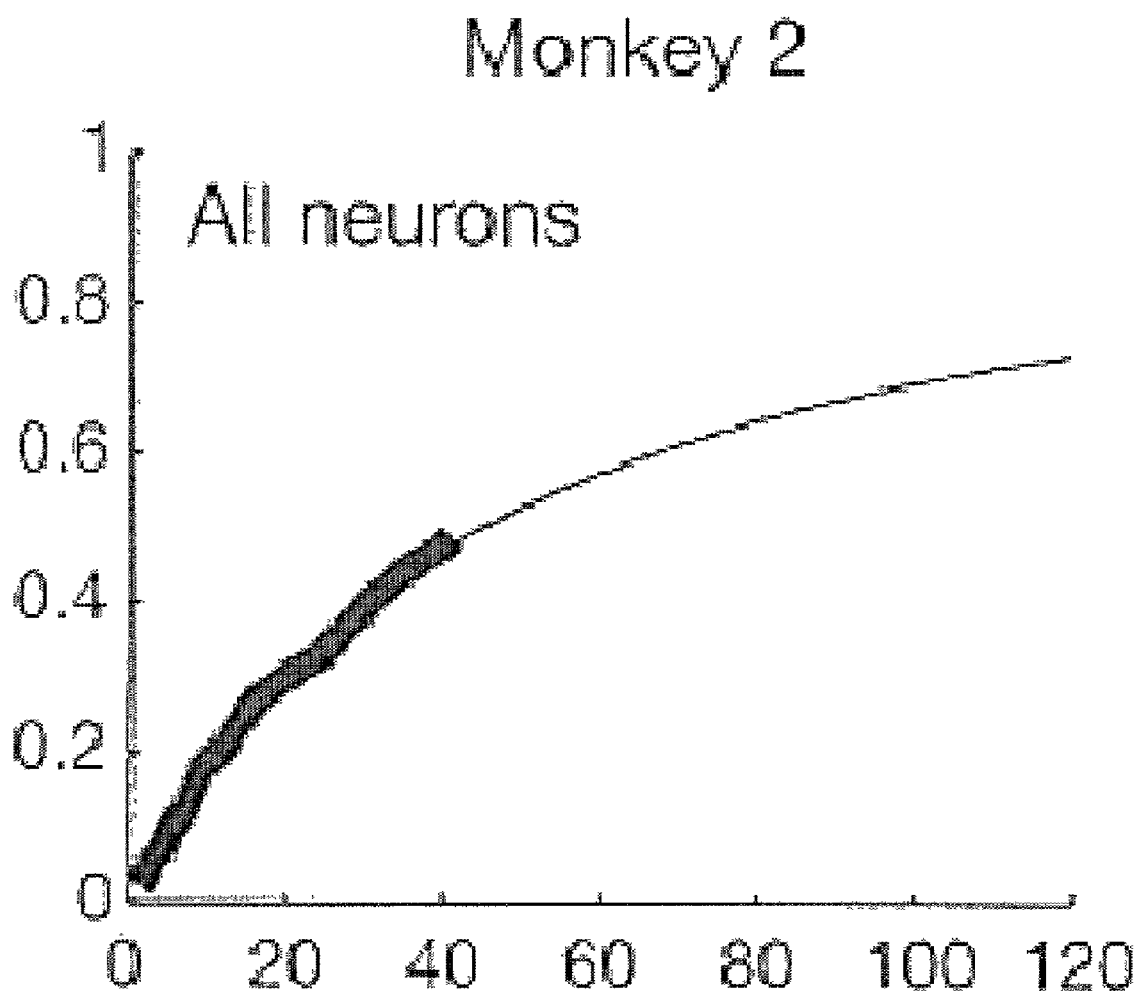
FIG. 4B is a plot depicting a neuron-dropping curve (black line) obtained in a singe session for all cortical neurons in Monkey 2, which is precisely fitted by a hyperbolic function (gray line).
Figure 4C:
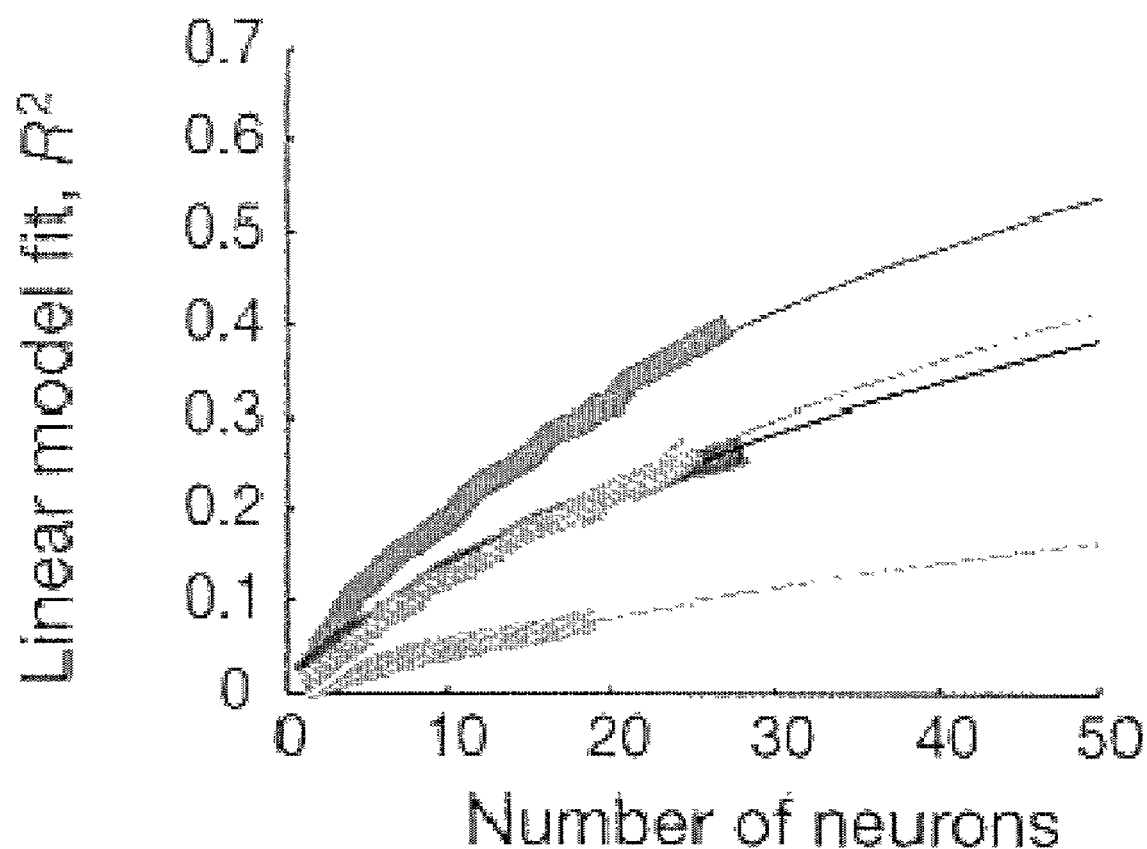
FIG. 4C is a plot depicting a neuron dropping curve (black line) and a corresponding hyperbolic function (gray line) for each cortical area of Monkey 1.
Figure 4D:
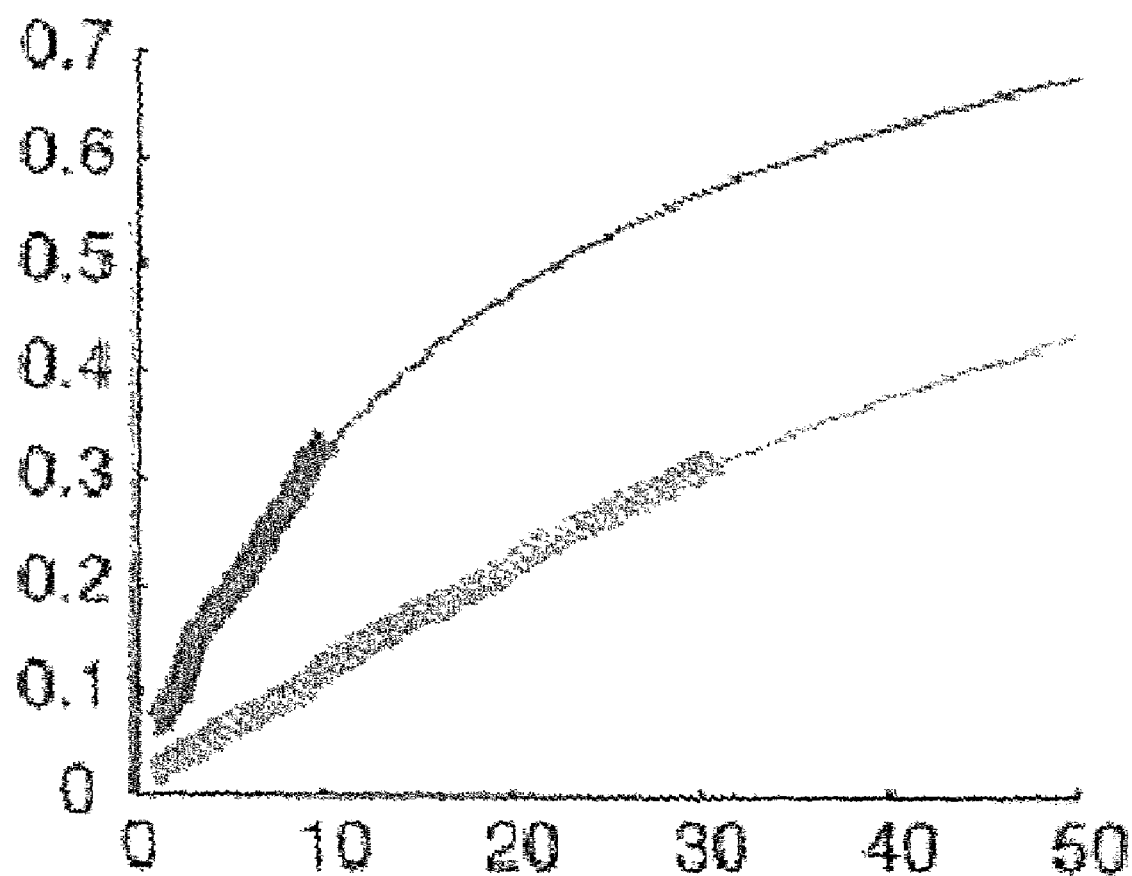
FIG. 4D is a plot depicting a neuron dropping curve (black line) and a corresponding hyperbolic function (gray line) for each cortical area of Monkey 2.
Figure 4E:
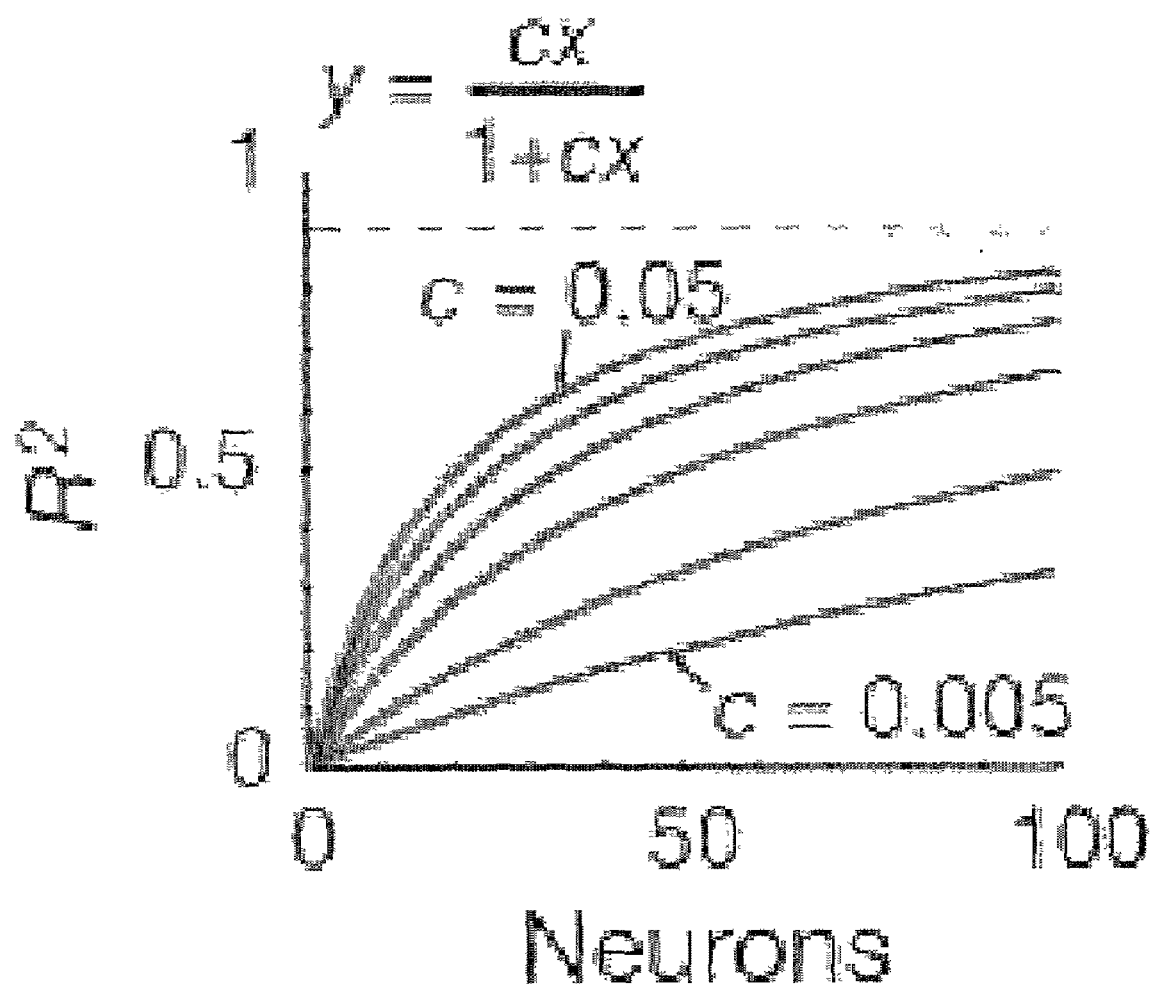
FIG. 4E is a plot depicting a range of hyperbolic functions, where x is the number of neurons and c is the fitted constant.
Figure 4F:
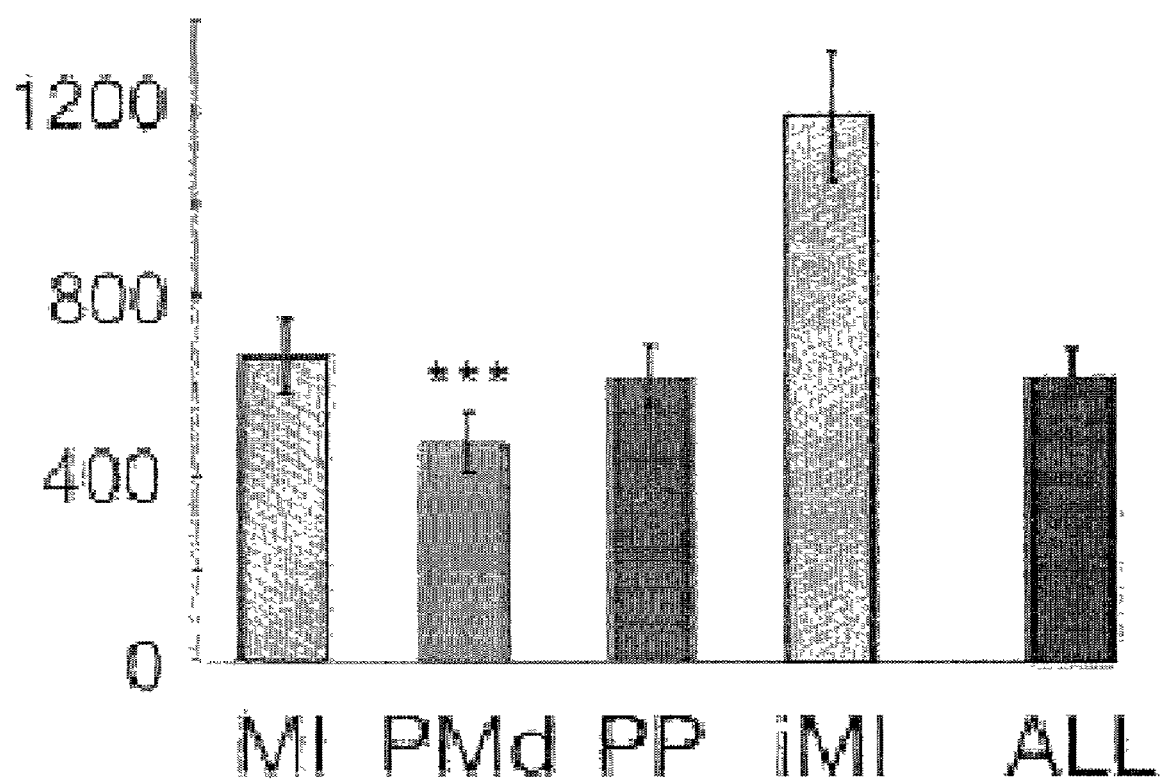
FIG. 4F is a bar graph depicting a n estimated number of neurons per cortical area required to reach an $R^2$ of 0.9 using the hyperbolic function in Money 1 and Monkey 2 (lower values represent higher mean contribution per neuron and three askerisks indicates $P<0.001$).
Figure 4G:
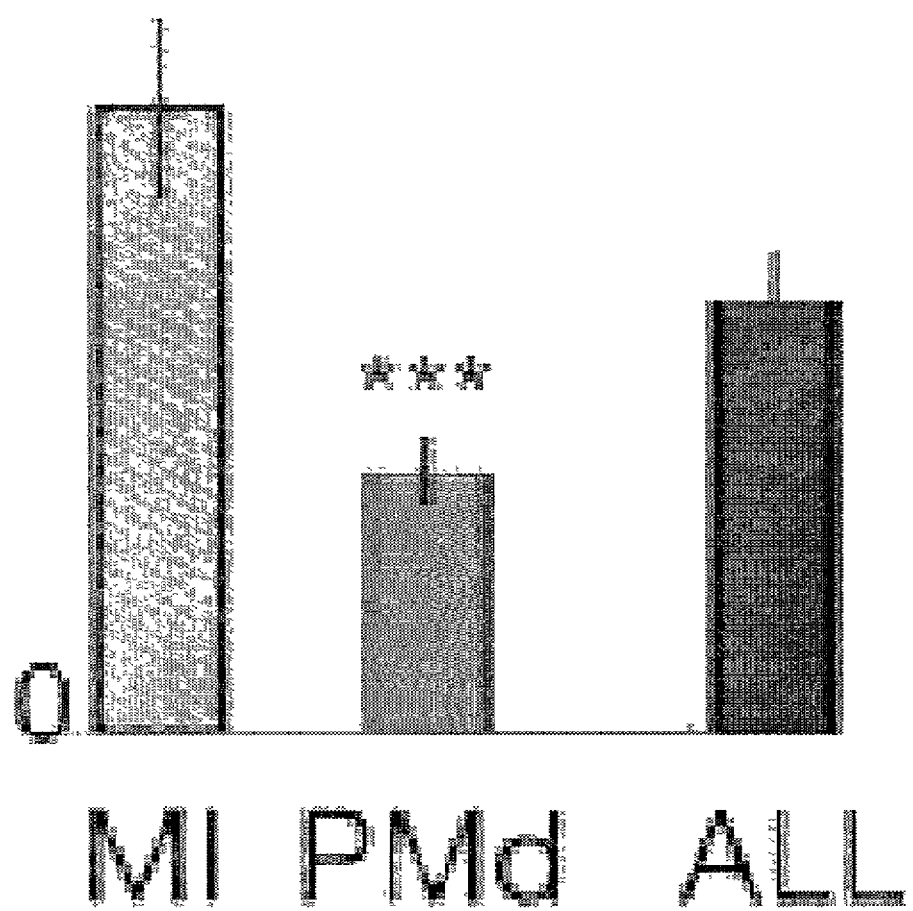
FIG. 4G is a bar graph depicting an estimated number of neurons per cortical area required to reach an $R^2$ of 0.9 using the hyperbolic function in Monkey 1 and Monkey 2 (lower values represent higher mean contribution per neuron and three askerisks indicates $P<0.001$).

It was then analyzed how each of the 2–4 different cortical areas contributed to the prediction of 1-D movements by calculating the average effect of removing individual neurons, one at a time, from the neuronal population used in each real-time session. This neuron dropping (ND) analysis was carried out independently for each of the cortical areas, as well as for the combination of all of them. We found that hyperbolic functions could fit (r range 0.996–0.9996) all curves that resulted from the ND analysis, using both the linear and ANN models in both animals. FIGS. 4A–4E illustrate typical ND curves and the corresponding hyperbolic fits. Extrapolations of the hyperbolic curves (FIG. 4F) revealed that 90% correct real-time prediction of 1-D movements could be theoretically achieved by applying the linear model to either 480±65.7 PMd neurons, 666±83.0 MI, 629±64.2 PP, or 1195±142 ipsi MI/PMd neurons in monkey 1 (average and S.E.M., 10 sessions). In monkey 2, the same level of accuracy would require either 376±42.3 PMd neurons or 869±127.4 MI neurons (FIG. 4G). Thus, in both monkeys, significantly fewer PMd (gray) neurons would theoretically be required to achieve the same level (90%) of 1-D hand movement prediction accuracy (p<0.001, Wilcoxon), i.e. on average, PMd neurons provided the highest contribution to the predictions. MI (gray line) and PP (black line) ensembles provided comparably lower contributions, while neurons located in the ipsilateral MI cortex accounted for the lowest amount of variance (light gray line). When all recorded cortical neurons were combined, the extrapolation of the hyperbolic functions produced identical theoretical estimates for 90% prediction accuracy in both monkeys (monkey 1=625±64 neurons; monkey 2=619±73 neurons, average and S.E.M.; p=0.70, Wilcoxon, n.s.).

These results are consistent with the hypothesis that most control signals for arm movements appear concurrently in large territories of the frontal and parietal cortices (Georgopoulos et al., (1982) *J. Neurosci.* 2: 1527–1537; Weinrich & Wise, (1982) *J. Neurosci.* 2: 1329–1345), and that, in theory, each of these cortical areas individually could be used to generate hand trajectory signals in real-time. However, the differences in estimated neuronal sample required to predict hand trajectories using a single cortical area likely reflect the functional specializations of these regions. Thus, the differences observed here are consistent with previous observations that PP and MI activity are influenced by motor parameters other than hand position (e.g. visual information, in the case of PP (Batista et al., (1999) *Science* 257–260; Feraina et al., (1997) *J. Neurophysiol.* 77: 1034–1038), or information related to the motor periphery in the case of MI (Mussa-Ivaldi, (1988) *Neurosci Lett.* 91: 106–111; Scott et al., (1997) *J. Neurophysiol.* 78: 2413–2426). Conceivably, the relative contributions of these cortical areas can also change according to such factors as the demands of the particular motor task, training level, or previous motor experience (Mitz et al., (1991) *J. Neurosci.* 11: 1855–1872; Laubach et al., (2000) *Nature* 405: 567–571).

DISCUSSION OF LABORATORY EXAMPLES 1–7

In conclusion, it was demonstrated that simultaneously recorded neural ensemble activity, derived from multiple cortical areas, can be used for the generation of both 1-D and 3-D signals to control robot movements in real-time. Contrary to previous off-line algorithms (Georgopoulos et al., (1982) *J. Neurosci.* 2: 1527–1537; Georgopoulos et al., (1986) *Science* 233: 1416–1419; Schwartz, (1994) *Science* 265: 540–542), the disclosed real-time approach did not make any a priori assumptions about either the physiological properties (e.g. shape of the tuning curve) of the single neurons, or the homogeneity of the neuronal population sample. Instead, by using random samples of cortical neurons accurate real-time predictions were obtained of both 1-D and 3-D arm movements. In this context, our findings support the notion that motor signals derived from ensembles of cortical neurons could be employed for long-term control of prosthetic limb movements (Schmidt, (1980) *Ann. Biomed. Eng.* 8: 339–349; Kennedy & Bakay, (1998) *Neuroreport* 9: 1701–1711). Indeed, the demonstration that chronically implanted microwires can yield reliable recordings in primates for at least 24 months demonstrates that the combination of denser multi-wire arrays with implantable integrated circuits, designed to handle all real-time signal processing and mathematical analysis, can form the basis of a brain-machine interface for allowing paralyzed patients to control voluntarily the movements of prosthetic limbs (Nicolelis, (2001) *Nature* 409: 403–407).

REFERENCES

The references listed below as well as all references cited in the specification are incorporated herein by reference to the extent that they supplement, explain, provide a background for or teach methodology, techniques and/or compositions employed herein.

Batista et al., (1999) *Science* 257–260
Bendat & Piersol, (1986) *Random Data. Analysis and Measurement Procedures*, Wiley, New York, N.Y.
Brillinger, (1981) *Time Series. Data Analysis and Theory*, Holden-Day, Dan Francisco, Calif.
Evarts, (1966) *J. Neurophysiol.* 29: 1011–1027
Feraina et al., (1997) *J. Neurophysiol.* 77: 1034–1038
Fetz & Cheney, (1980) *J. Neurophysiol.* 44: 751–772
Georgopoulos et al., (1982) *J. Neurosci.* 2: 1527–1537
Georgopoulos et al., (1986) *Science* 233: 1416–1419
Ghazanfar et al., (2000) *J. Neurosci.* 20: 3761–3775
Goulding, (1984) *Extended Physiological Taction, Design and Evaluation of a Sensory Feedback System for Myoelectric Control of a Terminal Device*, a thesis submitted to the faculty of the University of Utah, Department of Bioengineering
Halliday et al., (1995) *Prog. Biophys. Mol. Biol.* 64: 237–278
Humphrey et al., (1970) *Science* 170: 758–762
Kennedy & Bakay, (1998) *Neuroreport* 9: 1701–1711
Laubach et al., (2000) *Nature* 405: 567–571
Mitz et al., (1991) *J. Neurosci.* 11: 1855–1872
Mussa-Ivaldi, (1988) *Neurosci Lett.* 91: 106–111
Nicolelis et al., (1997) *Neuron* 18: 529–537
Nicolelis et al., (1998) *Nature Neurosci.* 1: 621–630
Nicolelis et al., (2000) *Nature* 408: 361–365
Nicolelis, (2001) *Nature* 409: 403–407
Powell, (1977) *Math. Program.* 12: 241–254
Preuss et al., (1996) *J. Comp. Neurol.* 371: 649–676
Schmidt, (1980) *Ann. Biomed. Eng.* 8: 339–349
Schwartz, (1994) *Science* 265: 540–542
Scott et al., (1997) *J. Neurophysiol.* 78: 2413–2426
Stepniewska et al., (1993) *J. Comp. Neurol.* 330: 567–571
Weinrich & Wise, (1982) *J. Neurosci.* 2: 1329–1345
Wise et al., (1997) *Annu. Rev. Neurosci.* 20: 25–42
U.S. Pat. No. 4,808,187
U.S. Pat. No. 5,336,269
U.S. Pat. No. 6,171,239

It will be understood that various details of the invention may be changed without departing from the scope of the invention. Furthermore, the foregoing description is for the purpose of illustration only, and not for the purpose of limitation—the invention being defined by the claims.

What is claimed is:

1. A real time closed loop brain-machine interface for restoring voluntary motor control and sensory feedback to a subject that has lost a degree of voluntary motor control and sensory feedback comprising:
   (a) an implantable microwire electrode array configured to be implantable into the subject's brain and adapted to acquire one or more brain-derived neural signals directly from the subject's brain;
   (b) an implantable neurochip adapted to communicate with the implantable microwire array and to filter and amplify the one or more neural signals;
   (c) a motor command extraction microchip adapted to communicate with the implantable neurochip and embodying one or more linear motor command extraction algorithms, the microchip and the algorithms adapted to extract motor commands from the brain-derived neural signals;

(d) an actuator adapted to communicate with the motor command extraction microchip and to move in response to the motor commands and to acquire sensory feedback information during and subsequent to a movement;

(e) a sensory feedback microchip embodying one or more sensory feed back information interpretation algorithms adapted to communicate with the actuator, the sensory feedback microchip adapted to form interpreted sensory feedback information;

(f) a structure adapted to communicate with the sensory feedback microchip and to wirelessly deliver interpreted sensory feedback information via electrical signals directly to the subject's brain through the implantable microwire electrode; and (g) one or more power sources adapted to provide power, as necessary, to one or more of the group comprising: the implantable neurochip; the motor command extraction microchip; the actuator; the sensory feedback microchip; and the structure adapted to relay interpreted sensory feedback information to the subject.

2. The real time closed loop brain-machine interface of claim 1, wherein the microwire electrode array comprises TEFLON® coated stainless steel microwires.

3. The real time closed loop brain-machine interface of claim 1, wherein the one or more motor command extraction algorithms comprise a linear model.

4. The real time closed loop brain-machine interface of claim 1, wherein the one or more motor command extraction algorithms comprise an artificial neural network.

5. The real time closed loop brain-machine interface of claim 1, wherein the motor command extraction microchip is implantable.

6. The real time closed loop brain-machine interface of claim 1, wherein the communication between the implantable neurochip and the motor command extraction microchip is wireless.

7. The real time closed loop brain-machine interface of claim 1, wherein the actuator comprises a prosthetic limb.

8. The real time closed loop brain-machine interface of claim 1, wherein the actuator comprises a device adapted to provide electrical stimulation of one or more muscles.

9. The real time closed loop brain-machine interface of claim 1, wherein the communication between the actuator and the motor command extraction microchip is wireless.

10. The real time closed loop brain-machine interface of claim 1, wherein the one or more sensory feedback interpretation algorithms is selected from the group consisting of linear and ANN algorithms.

11. A method of controlling an actuator adapted to provide sensory feedback to a subject by neural signals, the method comprising:

(a) collecting a neural signal directly from the brain of a subject through the implantable electrode implanted in the subject's brain;

(b) processing the neural signal to form a processed neural signal;

(c) extracting a motor command from the processed neural signal to form an extracted motor command, wherein the extracting employs a linear model;

(e) transmitting the extracted motor command to an actuator, whereby the actuator effects a movement;

(f) acquiring sensory feedback information from the actuator;

(g) interpreting the sensory feedback information to form interpreted sensory feedback information; and (h) relaying the interpreted sensory feedback information wirelessly via electrical signals directly to the subject's brain through the implantable electrode.

12. The method of claim 11, wherein the neural signal is an electrical signal.

13. The method of claim 12, wherein the extracting comprises applying an artificial neural network to the processed neural signals.

14. The method of claim 11, wherein the neural signal is acquired via plurality of electrodes comprising one or more microwires.

15. The method of claim 14, wherein the microwires comprise a material selected from the group consisting of stainless steel, platinum and tungsten.

16. The method of claim 14, wherein the diameter of the one or more microwires is about 50 µm.

17. The method of claim 14, wherein the microwires are TEFLON® coated.

18. The method of claim 14, wherein the one or more microwires are oriented in a definite spatial relationship relative to one another to thereby form a microwire array.

19. The method of claim 18, wherein the microwires comprise a material selected from the group consisting of stainless steel, platinum and tungsten.

20. The method of claim 18, wherein the diameter of the one or more microwires is about 25 to 50 µm.

21. The method of claim 18, wherein the microwires are TEFLON® coated.

22. The method of claim 18, wherein the microwire array comprises about 16 to 128 microwires.

23. The method of claim 14, wherein the one or more microwires are oriented in a definite spatial relationship relative to one another to thereby form a microwire bundle.

24. The method of claim 23, wherein the microwires comprise a material selected from the group consisting of stainless steel, platinum and tungsten.

25. The method of claim 23, wherein the diameter of the one or more microwires is about 25 to 50 µm.

26. The method of claim 23, wherein the microwires are TEFLON® coated.

27. The method of claim 23, wherein the microwires have different lengths.

28. The method of claim 23, wherein the difference in length between a first wire tip and a second wire tip is about 150 to 300 µm.

29. The method of claim 11, wherein the collecting is performed in real time.

30. The method of claim 11, wherein the processing comprises:

(a) amplifying the one or more neural signals to form amplified neural signals;

(b) filtering the amplified neural signals to form filtered neural signals; and (c) performing a spike detection analysis on the filtered neural signals.

31. The method of claim 11, wherein the processing is performed in real time.

32. The method of claim 11, wherein the extracting comprises applying a linear model to the processed neural signals.

33. The method of claim 11, wherein the extracting is performed in real time.

34. The method of claim 11, wherein the transmitting comprises conveying the extracted motor commands wirelessly.

35. The method of claim 11 wherein the transmitting comprises conveying the extracted motor commands over a cable.

36. The method of claim 11, wherein the transmitting is performed in real time.

37. The method of claim 11, wherein the sensory information is selected from the group consisting of tactile information, temperature information and visual information.

38. The method of claim 11, wherein the sensory feedback information is acquired in real time.

39. A method of imparting voluntary motor control and sensory feedback to a subject that has lost a degree of voluntary motor control and sensory feedback, the method comprising:
  (a) implanting a neural signal acquisition apparatus in the subject's brain;
  (b) fitting the subject with an actuator adapted to respond to neural signals with movement and to acquire sensory feedback;
  (c) collecting one or more neural signals directly from the brain of the subject;
  (d) extracting one or more motor commands from the acquired neural signals to form extracted motor commands, wherein the extracting employs a linear model;
  (e) transmitting the extracted motor commands to the actuator;
  (f) effecting a movement corresponding to the extracted motor commands;
  (g) acquiring sensory feedback information via the actuator;
  (h) interpreting the sensory feedback information to form interpreted sensory feedback information; and
  (i) relaying the interpreted sensory feedback information wirelessly via electrical signals directly to the subject's brain through the neural signal acquisition apparatus, whereby voluntary motor control and sensory feedback is imparted to a subject that has lost a degree of voluntary motor control and sensory feedback.

40. The method of claim 39, wherein the neural signal acquisition apparatus comprises:
  (a) a plurality of electrodes; and
  (b) a neurochip adapted to amplify and filter neural signals the neurochip adapted to communicate with the plurality of electrodes.

41. The method of claim 40, wherein the plurality of electrodes comprises one or more microwire electrode arrays.

42. The method of claim 40, wherein the plurality of electrodes comprises one or more microwire bundles.

43. The method of claim 39, wherein the neural signals comprise electrical signals.

44. The method of claim 39, wherein the collecting is performed in real time.

45. The method of claim 39, wherein the actuator comprises a prosthetic limb.

46. The method of claim 39, wherein the actuator comprises a device adapted to provide electrical stimulation of one or more muscles.

47. The method of claim 39, wherein the fitting comprises interfacing the actuator with the central nervous system of the subject.

48. The method of claim 39, wherein the extracting comprises passing the one or more acquired neural signals through a linear model.

49. The method of claim 39, wherein the extracting comprises passing the one or more acquired neural signals through an artificial neural network.

50. The method of claim 39, wherein the transmitting comprises conveying the extracted motor commands wirelessly.

51. The method of claim 39, wherein the transmitting comprises conveying the extracted motor commands over a cable.

52. The method of claim 39, wherein the effected movement comprises a motion in three-dimensions.

53. The method of claim 39, wherein the movement effecting is performed in real time.

54. The method of claim 39, wherein the sensory feedback information comprises information selected from the group consisting of tactile information, temperature information and visual information.

55. The method of claim 39, wherein the acquiring is performed by one or more sensor mechanisms disposed on the actuator.

56. The method of claim 55, wherein the one or more sensor mechanisms comprise one or more devices adapted to provide one or more of visual and tactile feedback information.

57. The method of claim 39, wherein the interpreting comprises performing one of a linear algorithm and an ANN algorithm.

58. The method of claim 39, wherein the interpreting is performed by one or more algorithms embodied on an implanted microchip.

59. The method of claim 39, wherein the interpreting is performed by one or more algorithms embodied on the actuator.

60. The method of claim 39, wherein the interpreting is performed in real time.

61. The method of claim 39, wherein the relaying is performed in real time.

62. The method of claim 39, wherein the steps (a) through (i) are performed in real time.

* * * * *